United States Patent
Brus et al.

(10) Patent No.: US 10,071,964 B2
(45) Date of Patent: Sep. 11, 2018

(54) DISUBSTITUTED PIPERIDINES AS BUTYRYLCHOLINESTERASE INHIBITORS

(71) Applicant: Univerza V Ljubljani, Ljubljani (SI)

(72) Inventors: Boris Brus, Vojnik (SI); Urban Kosak, Ljubljana (SI); Damijan Knez, Vuzenica (SI); Nicolas Coquelle, Grenoble (FR); Jacques-Philippe Colletier, Grenoble (FR); Stanislav Gobec, Ljubljana (SI)

(73) Assignee: UNIVERZA V LJUBJIANI, Ljubliana (SI)

( * ) Notice: Subject to any disclaimer, the term of this patent is extended or adjusted under 35 U.S.C. 154(b) by 0 days.

(21) Appl. No.: 15/560,580

(22) PCT Filed: Mar. 22, 2016

(86) PCT No.: PCT/IB2016/051603
§ 371 (c)(1),
(2) Date: Sep. 22, 2017

(87) PCT Pub. No.: WO2016/151484
PCT Pub. Date: Sep. 29, 2016

(65) Prior Publication Data
US 2018/0086707 A1  Mar. 29, 2018

(30) Foreign Application Priority Data
Mar. 25, 2015 (SI) .................. P-201500076

(51) Int. Cl.
| | |
|---|---|
| *A61K 31/445* | (2006.01) |
| *C07D 211/06* | (2006.01) |
| *C07D 211/28* | (2006.01) |
| *A61K 31/4523* | (2006.01) |
| *A61K 31/453* | (2006.01) |
| *A61K 31/4709* | (2006.01) |
| *C07D 401/12* | (2006.01) |
| *C07D 405/12* | (2006.01) |
| *C07D 211/26* | (2006.01) |

(52) U.S. Cl.
CPC .......... *C07D 211/28* (2013.01); *A61K 31/445* (2013.01); *A61K 31/453* (2013.01); *A61K 31/4523* (2013.01); *A61K 31/4709* (2013.01); *C07D 211/26* (2013.01); *C07D 401/12* (2013.01); *C07D 405/12* (2013.01)

(58) Field of Classification Search
CPC ............................ A61K 31/445; C07D 211/06
USPC .......................................... 514/315; 546/246
See application file for complete search history.

(56) References Cited

FOREIGN PATENT DOCUMENTS

WO   WO 16/151484   *   9/2016

OTHER PUBLICATIONS

Jordan, V. C. Nature Reviews: Drug Discovery, 2, 2003, 205.*
Hackam, et al. JAMA, 296(14), 2006, 1731-1732.*
Ballard et al., "Cholinesterases: Roles in the Brain During Health and Disease" Current Alzheimer Research, vol. 2, pp. 307-318, 2005.
Bar-On et al., "Kinetic and Structural Studies on the Interaction of Cholinesterases with the Anti-Alzheimer Drug Rivastigmine" Biochemistry, vol. 41, pp. 3555-3564, 2002.
Bartus et al., "The Cholinergic Hypothesis of Geriatric Memory Dysfunction" Science, vol. 217, Issue 4558, pp. 408-417, Jul. 30, 1982.
Bartus, "On Neurodegenerative Diseases, Models, and Treatment Strategies: Lessons Learned and Lessons Forgotten a Generation Following the Cholinergic Hypothesis" Experimental Neurology, vol. 163, pp. 495-529, 2000.
Bevc et al., "ENZO: A Web Tool for Derivation and Evaluation of Kinetic Models of Enzyme Catalyzed Reactions" PLoS one, vol. 6, Issue 7, e22265, Jul. 2011.
Bowen et al., "Neurotransmitter-Related Enzymes and Indices of Hypoxia in Senile Dementia and Other Abiotrophies" Brain, vol. 99, pp. 459-496, 1976.
Brus et al., "Discovery, Biological Evaluation, and Crystal Structure of a Novel Nanomolar Selective Butyrylcholinesterase Inhibitor" Journal of Medicinal Chemistry, vol. 57, pp. 8167-8179, Sep. 16, 2014.
Carolan et al., "Isosorbide-2-carbamate Esters: Potent and Selective Butyrylcholinesterase Inhibitors" J. Med. Chem., vol. 51, pp. 6400-6409, 2008.
Ciro et al., "Biochemical Differentiation of Cholinesterases from Normal and Alzheimer's Disease Cortex" Curr Alzheimer Res. vol. 9(1), pp. 138-143, Jan. 1, 2012.

(Continued)

*Primary Examiner* — Douglas M Willis
(74) *Attorney, Agent, or Firm* — Heslin Rothenberg Farley & Mesiti P.C.

(57) ABSTRACT

This invention relates to new inhibitors of butyrylcholinesterase with general formulas I and II, where substituents are described in patent description. Compounds can be in the form of pure enantiomers or as racemic mixtures, or in the form of pharmaceutically acceptable salts. The present invention relates to the use of these inhibitors for the treatment of Alzheimer's disease and other forms of dementia.

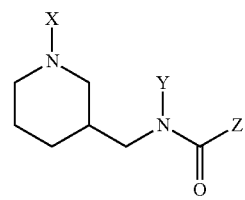

(I)

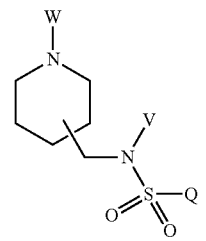

(II)

19 Claims, No Drawings

(56) References Cited

OTHER PUBLICATIONS

Citron, "Alzheimer's Disease: Strategies for Disease Modification" Nature Reviews, vol. 9, pp. 387-398, May 2010.
Darvesh et al. "Selective Reversible Inhibition of Human Butyrylcholinesterase by Aryl Amide Derivatives of Phenothiazine" Bioorganic & Medicinal Chemistry, vol. 15, pp. 6367-6378, 2007.
Davies et al., "Selective Loss of Central Cholinergic Neurons in Alzheimer's Disease" The Lancet, p. 1403, Dec. 25, 1976.
Decker et al., "Novel Tricyclic Quinazolinimines and Related Tetracyclic Nitrogen Bridgehead Compounds as Cholinesterase Inhibitors with Selectivity Towards Butyrylcholinesterase" Bioorganic & Medicinal Chemistry, vol. 14, pp. 1966-1977, 2006.
Drachman et al., "Human Memory and the Cholinergic System, A Relationship to Aging?" Arch Neurol, vol. 30, pp. 113-121, Feb. 1974.
Ellman et al., "A New and Rapid Colorimetric Determination of Acetylcholinesterase Activity" Biochemical Pharmacology, vol. 7, pp. 88-95, 1961.
Fisher, "Therapeutic Strategies in Alzheimer's Disease: M1 Muscarinic Agonists" Jpn. J. Pharmacol, vol. 84, pp. 101-112, 2000.
Furukawa-Hibi et al., "Butyrylcholinesterase Inhibitors Ameliorate Cognitive Dysfunction Induced by Amyloid-β Peptide in Mice" Behav. Brain Res., vol. 225(1), pp. 222-229, Nov. 20, 2011.
Giacobini, "Cholinergic Function and Alzheimer's Disease" Int. J. Geriatr. Psychiatry, vol. 18, pp. S1-S5, 2003.
Giacobini, "Cholinesterase Inhibitors: New Roles and Therapeutic Alternatives" Pharmacological Research, vol. 50, pp. 433-440, 2004.
Greenblatt et al., "Structure of Acetylcholinesterase Complexed with (−)-Galanthamine at 2.3 Å Resolution" FEBS Letters, vol. 463, pp. 321-326, 1999.
Greig et al., "Selective Butyrylcholinesterase Inhibition Elevates Brain Acetylcholine, Augments Learning and Lowers Alzheimer β-amyloid Peptide in Rodent" PNAS, vol. 102, No. 47, pp. 17213-17218, Nov. 22, 2005.
Hartmann et al., "Excessive Hippocampal Acetylcholine Levels in Acetylcholinesterase-Deficient Mice are Moderated by Butyrylcholinesterase Activity" Journal of Neurochemistry, vol. 100, pp. 1421-1429, 2007.
Holmes et al. "Rate of Progression of Cognitive Decline in Alzheimer's Disease: Effect of Butyrylcholinesterase K Gene Variation" J. Neurol Neurosurg Psychiatry, vol. 76, pp. 640-643, 2005.
Karlsson et al., "Identification and Characterization of Diarylimidazoles as Hybrid Inhibitors of Butyrylcholinesterase and Amyloid Beta Fibril Formation" European Journal of Pharmaceutical Sciences, vol. 45, pp. 169-183, 2012.
Kawakami et al., "The Rationale for E2020 as a Potent Acetylcholinesterase Inhibitor" Bioorganic & Medicinal Chemistry, vol. 4, No. 9, pp. 1429-1446, 1996.
Košak et al., "Straightforward Synthesis of Orthogonally Protected Piperidin-3-ylmethanamine and Piperidin-4-ylmethanamine Derivatives" Tetrahedron Letters, vol. 55, pp. 2037-2039, 2014.
Law et al., "Dialkyl Phenyl Phosphates as Novel Selective Inhibitors of Butyrylcholinesterase" Biochemical and Biophysical Research Communications, 355, pp. 371-378, 2007.
Li et al., "Production of the Butyrylcholinesterase Knockout Mouse" Journal of Molecular Neuroscience, vol. 30, pp. 193-195, 2006.
McGleenon et al., "Acetylcholinesterase Inhibitors in Alzheimer's Disease" Br. J. Clin. Pharmacol, vol. 48, pp. 471-480, Jun. 1999.
Nawaz et al., "Cation-π and π-π Stacking Interactions Allow Selective Inhibition of Butyrylcholinesterase by Modified Quinine and Cinchonidine Alkaloids" Biochemical and Biophysical Research Communications, vol. 404, pp. 935-940, 2011.
Nicolet et al., "Crystal Structures of Human Butyrylcholinesterase and of Its Complexes with Substrate and Products" The Journal of Biological Chemistry, vol. 278, No. 42, pp. 41141-41147, Oct. 17, 2003.
Perry et al., "Changes in Brain Cholinesterases in Senile Dementia of Alzheimer Type" Neuropathology and Applied Neurobiology, vol. 4, pp. 273-277, 1978.
Perry et al., "Correlation of Cholinergic Abnormalities with Senile Plaques and Mental Test Scores in Senile Dementia" British Medical Journal, vol. 2, pp. 1457-1459, Nov. 25, 1978.
Picciotto et al., "Nicotinic Receptors in Aging and Dementia" J Neurobiol, vol. 53, pp. 641-655, 2002.
Querfurth et al., "Alzheimer's Disease" The New England Journal of Medicine, vol. 362, pp. 329-344, Jan. 28, 2010.
Rivera-Becerril et al., "Synthesis and Biological Evaluation of (−)- and (+)-Debromoflustmmine B and Its Analogues as Selective Butyrylcholinesterase Inhibitors" J. Med. Chem., vol. 51, pp. 5271-5284, 2008.
Rizzo et al., "Benzofuran-Based Hybrid Compounds for the Inhibition of Cholinesterase Activity, β Amyloid Aggregation, and Aβ Neurotoxicity" J. Med. Chem., vol. 51, pp. 2883-2886, 2008.
Rylett et al., "Evidence for High Affinity Choline Transport in Synaptosomes Prepared from Hippocampus and Neocortex of Patients with Alzheimer's Disease" Brain Research, vol. 289, pp. 169-175, 1983.
Savini et al., "Novel and Potent Tacrine-Related Hetero- and Homobivalent Ligands for Acetylcholinesterase and Butyrylcholinesterase" Bioorganic & Medicinal Chemistry Letters, vol. 11, pp. 1779-1782, 2011.
Summers et al., "Oral Tetrahydroaminoacridine in Long-Term Treatment of Senile Dementia, Alzheimer Type" The New England Journal of Medicine, vol. 315, No. 20, Nov. 13, 1986.
Wanibuchi et al., "Characterization of a Novel Muscarinic Receptor Agonist, YM796: Comparison with Cholinesterase Inhibitors in in Vivo Pharmaceutical Studies" European Journal of Pharmacology, vol. 265, pp. 151-158, 1994.
Whitehouse et al., "Alzheimer's Disease and Senile Dementia: Loss of Neurons in the Basal Forebrain" Science, vol. 215, Mar. 5, 1982.
Yu et al., "Synthesis of Novel Phenserine-Based-Selective Inhibitors of Butyrylcholinesterase for Alzheimer's Disease" J. Med. Chem. vol. 42, pp. 1855-1861, 1999.
Yu et al., "Synthesis of 4-[(diethylamino)methyl]-phenol Derivatives as Novel Cholinesterase Inhibitors with Selectivity Towards Butyrylcholinesterase" Bioorganic & Medicinal Chemistry Letters, vol. 20, pp. 3254-3258, 2010.
Chemical Abstracts Service, Columbus, Ohio, Aug. 2, 2012, XP002759021.
Chemical Abstracts Service, Columbus, Ohio, Nov. 24, 2011, XP002759026.
Damijan Knez et al., "Structure-based development of nitroxoline derivatives as potential multifunctional anti-Alzheimer agents", Bioorganic & Medicinal Chemistry, vol. 23, No. 15, pp. 4442-4452, Jun. 14, 2015.
Chemical Abstracts Service, Columbus, Ohio, Nov. 13, 2007, XP002759017.
Chemical Abstracts Service, Columbus, Ohio, Nov. 11, 2007, XP002759018.
Chemical Abstracts Service, Columbus, Ohio, Nov. 2, 2008, XP002759019.
Chemical Abstracts Service, Columbus, Ohio, Dec. 21, 2008, XP002759020.
Chemical Abstracts Service, Columbus, Ohio, Aug. 15, 2011, XP002759022.
Chemical Abstracts Service, Columbus, Ohio, Mar. 10, 2010, XP002759023.
Chemical Abstracts Service, Columbus, Ohio, Apr. 29, 2011, XP002759024.
Chemical Abstracts Service, Columbus, Ohio, May 1, 2011, XP002759025.

* cited by examiner

DISUBSTITUTED PIPERIDINES AS BUTYRYLCHOLINESTERASE INHIBITORS

CROSS REFERENCE TO RELATED APPLICATIONS

This application is a U.S. National Phase filing under 35 U.S.C. § 371 of International Application PCT/IB2016/051603, filed Mar. 22, 2016, and published as WO 2016/151484 A1 on Sep. 29, 2016. PCT/IB2016/051603 claims priority from Slovenian application number P-201500076, filed Mar. 25, 2015. The entire contents of each of these applications are hereby incorporated herein by reference.

FIELD OF THE INVENTION

The present invention relates to the field of medicinal chemistry and novel 1,3- in 1,4-disubstituted derivatives of piperidine as pharmaceutical active compounds. These compounds can be in the form of a mixture of enantiomers or in the form of pure enantiomers, in the form of pharmaceutically acceptable salts, as hydrates or solvates thereof. Novel 1,3- and 1,4-disubstituted derivatives of piperidine are inhibitors of the enzyme butyrylcholinesterase. The compounds of the present invention are useful for the treatment of various diseases which may be therapeutically modified by altering the activity of butyrylcholinesterase such as Alzheimer's disease and other dementias.

DESCRIPTION OF RELATED ART

Alzheimer's disease (AD) is a progressive neurodegenerative disorder of central nervous system (CNS), which results in the death of neurons and loss of CNS function. AD is a leading cause of dementia (60-80%). Symptoms of advanced AD include weakened communication, bad judgment, confusion, behavioral changes and problems with speech, swelling and walk. Despite severe loss of memory, patients completely deny the symptoms and are fully dependent on the care of relatives in the last stages of the disease (24/7 care).

The time from the diagnosis to death varies from 1 to 25 years with an average of 10 years. The death is a consequence of several complications, which include infections, such as infections of bedsores that occur when people stay in bed for prolonged periods. Alzheimer's patients also may have difficulty swallowing, and they may inhale food, which can result in aspiration pneumonia. Alzheimer's patients also can develop fatal blood clots. (Citron M. Nat. Rev. Drug Discov. 2010, 9, 387-398; Querfurth H. W. and LaFerla F. M. N. Engl. J. Med. 2010, 362, 329-344) Despite intensive investigations, the exact mechanism of AD pathogenesis is not yet entirely understood. Several different factors are known to contribute to AD progression. This theory has been proven by the post mortem analysis of the AD patients' brains, which revealed the death of cholinergic neurons, senile plaques and extracellular deposits of amyloid beta (Aβ), neurofibrillary tangles composed from abnormal filaments of tau protein and the imbalance of the metal ions in the areas of brain responsible for the memory formation. These findings led to the formation of several hypotheses with the aim to describe the AD pathophysiology.

Acetylcholine (ACh) is a cholinergic neurotransmitter in the peripheral nervous system (PNS) and in the CNS synthesized by the enzyme choline-acetyltransferase (ChAT). Several studies on humans and on primates confirmed the important role of ACh in the process of learning and memory formation (Drachman D. A. and Leavitt J. Arch Neurol. 1974, 30, 113-121). Furthermore, systematic investigation of AD patients revealed: i) loss of cholinergic activity (decreased ACh concentrations) in brains, (Davies P. and Maloney A. J. Lancet 1976, 25, 1403; Perry E. K. at al. Neuropathol. Appl. Neurobiol. 1978, 4, 273-277) ii) decreased ChAT activity in cortex and hippocampus, (Bowen D. M. et al. Brain 1976, 99, 459-496; Perry E. K. et al. Br. Med. J. 19798, 2, 1457-1459) iii) decrease of high-affinity choline transport, (Rylett R. J. et al. Brain Res. 1983, 289, 169-175) and iv) degeneration of cholinergic neurons, which project from Meynert's nuclei into cortex, striatum and hippocampus. (Whitehouse P. J. et al. Science 1982, 215, 1237-1239) The results of these studies led to the formation of cholinergic hypothesis of AD stating that the loss of cholinergic neurons in the basal forebrain and the associated low levels of neurotransmitter acetylcholine in the cerebral cortex and other areas contribute significantly to severe memory and learning deficits associated with AD patients. (Bartus R. T. et al. Science 1982, 217, 408-414; Bartus R. T. et al. Exp. Neurol. 2000, 163, 495-529) At the neuronal level, cholinergic neurotransmission is regulated by two types of cholinesterases (ChEs): acetylcholinesterase (AChE) and butyrylcholinesterase (BChE). ChEs are enzymes responsible for the ACh hydrolysis to yield acetate and choline. BChE and AChE share the backbone structure and their tertiary structure is nearly identical, while the difference is observed in the area of acyl-binding pocket. The corresponding pocket in BChE is significantly greater in size, which allows the binding of bigger ligands. (Nicolet Y. et al. J. Biol. Chem. 2003, 278, 41141-41147) In the brain of healthy adults, AChE accounts for 80% of the ChE activity, with BChE accounting for the remainder. However, the assumed co-regulatory function of BChE in termination of cholinergic neurotransmission in the healthy brain changes in brains of patients with progressive AD, where the levels of AChE and ChAT are reduced to 55% to 67% of normal levels. Lowered AChE and ChAT activity in cortex of patients do not cause death, yet do not sustain the normal brain functioning anymore. Studies revealed the opposite for BChE, where its cortical levels and expression show a significant increase in the late stages of AD, with the ratio between BChE and AChE changing from 0.2 (healthy brains) up to as much as 11 (AD brains). (Ciro A. et al. Curr. Alzheimer Res. 2012, 9, 138-143; Giacobini, E. Int. J. Geriat. Psychiatry 2003, 18, S1-S5) The altered ratio is implicating a shift from supportive to leading role of BChE in hydrolyzing excess Ach. Further experiments revealed that: i) BChE knock-out mice do not show physiological disadvantages, (Li B. et al. J. Mol. Neurosci. 2006, 30, 193-195) ii) AD patients with BChE mutations express slower decrease of cognitive abilities, (Holmes C. et al. 2005 J. Neurol. Neurosurg. Psychiatry, 76, 640-643) and iii) selective BChE inhibitors can raise ACh levels in the brain and improve cognitive performance in mice AD models, (Furukawa-Hibi Y. et al. Behav. Brain Res. 2011, 225, 222-229; Greig, N. H. PNAS 2005, 102, 17213-17218; Hartmann, J. et al. J. Neurochem. 2007, 100, 1421-1429) without any adverse parasympathetic side effects, which limits the doses of AChE inhibitors that can be administered. (Ballard C. at al. Curr. Alzheimer Res. 2005, 2, 307-318; Giacobini E. Pharmacol. Res. 2004, 50, 433-440) Altogether, these data suggest that BChE is an important therapeutic target for restoring ACh levels in the brain and thus improving the symptoms of advanced AD, where selective BChE inhibition seems even more reasonable than the AChE inhibition alone.

Cholinergic hypothesis inspired the developments of ligands capable of increasing cholinergic transmission. This strategy includes the agonists of muscarinic ACh receptors type M, (Fisher A. Jap. J. Pharmacol. 2000, 84, 101-112; Wanibuchi F. et al. Eur. J. Pharmacol. 1994, 265, 151-158) agonists of nicotinic ACh receptors, (Picciotto M. R. and Zoli M. J. Neurobiol. 2002, 53, 641-655) and AChE inhibitors (AChEi), which resulted in first approved drugs for the symptomatic treatment of AD. Recently, four drugs entered the market, which target mainly AChE: donepezil, (Kawakami Y. et al. Bioorg. Med. Chem. 1996, 4, 1429-1446) rivastigmine, (Bar-On P. et al. Biochemistry (Mosc.) 2002, 41, 3555-3564) tacrine (Summers W. K. at al. N. Engl. J. Med. 1986, 315, 1241-1245) and alkaloid galantamine. (Greenblatt, H. M. et al. FEBS Lett. 1999, 463, 321-326) Several selective BChE inhibitors have already been described, which are analogues of: cymserine, (Yu Q. et al, J. Med. Chem. 1999, 42, 1855-1861) phenothiazine, (Darvesh S. et al. Bioorg. Med. Chem. 2007, 15, 6367-6378) tacrine, (Savini L. et al. Bioorg. Med. Chem. Lett. 2001, 9, 1779-1782) quinazolinimine, (Decker M. et al. Bioorg Med Chem. 2006, 14, 1966-1977) isosorbide, (Carolan C. G. et al. J. Med. Chem. 2008, 51, 6400-6409) 4-[(diethylamino)methyl]-phenol, (Yu L. et al. Bioorg. Med. Chem. Lett. 2010, 20, 3254-3258) debromoflustramine B, (Rivera-Becerril et al. J. Med. Chem. 2008, 51, 5271-5284), dialkyl phenyl phosphate, (Law K. S. et al. Biochem. Biophys. Res. Commun. 2007, 355, 371-278) diarylimidazole, (Karlsson D. et al. Eur. J. Pharm Sci. 2012, 45, 169-183) benzofuran, (Rizzo S. et al. J. Med. Chem. 2008, 51, 2883-2886) and quinine (Nawaz S. A. et al. Biochem. Biophys. Res. Commun. 2011, 404, 935-940). Selective BChE inhibitors raise ACh levels in brains without peripheral (parasympathomimetic) side effects, which limits the dosing of the approved AChE inhibitors. (McGleenon B. M. et al. Br. J. Clin. Pharmacol. 1999, 48, 471-480)

BRIEF SUMMARY OF THE INVENTION

The invention relates to novel inhibitors of the enzyme butyrylcholinesterase with the general formula I and II, where substituents are clearly defined in the form of pure enantiomers or mixture of enantiomers and their pharmaceutically acceptable salts. Invention relates to the use of the described compounds for the treatment of Alzheimer's disease and other dementias.

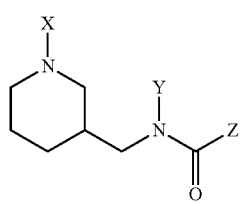

(I)

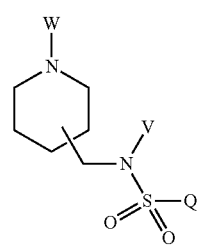

(II)

Technical Problem

Several medications are approved for the treatment of Alzheimer's disease, which act as an acetylcholinesterase inhibitors or N-methyl-aspartate (NMDA) receptors antagonists. These medications cause several side effects with limited effectiveness. Therefore, there is a constant need for the discovery of novel medications for the treatment of Alzheimer's disease.

DETAILED DESCRIPTION OF THE INVENTION

The invention describes the compounds having general formula (I),

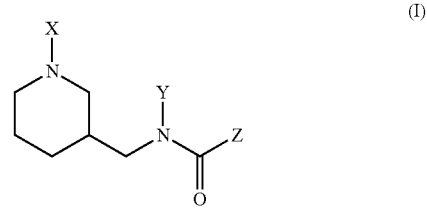

(I)

wherein the substituents are the following:
X: —CH$_2$-Ph,

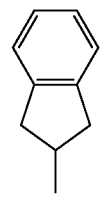

Y: —CH$_2$—CH$_2$—NMe$_2$, —CH$_2$—CH$_2$—CH$_2$—NMe$_2$
Z:

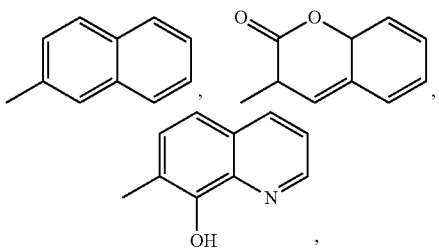

and compounds having general formula (II)

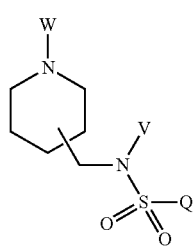

(II)

where the piperidine scaffold is 1,3- and 1,4-disubstituted, wherein the substituents are the following:

W:

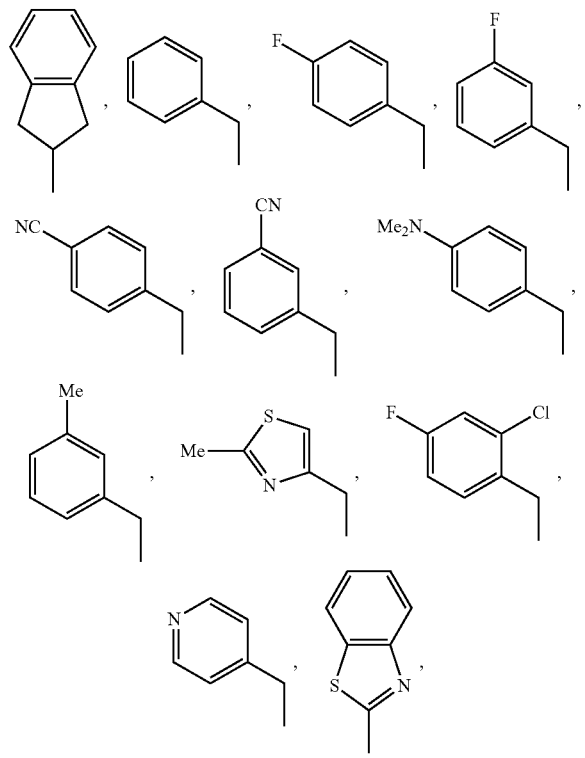

V: H, Me, Et, n-Pr, n-Bu, —CH$_2$—CH$_2$—OMe, —CH$_2$—CH$_2$—CH$_2$—OMe,

Q:

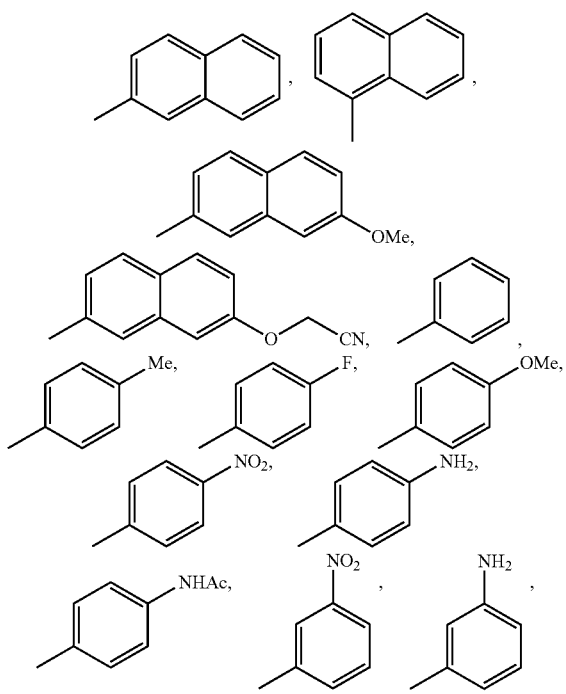

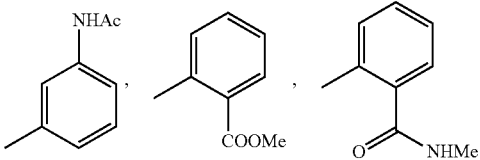

Some compounds from this invention possess stereogenic center with an absolute configuration of R or S. The compounds can appear in a racemic form, in a form of pure enantiomers or in the form of conglomerates.

The invention further relates to the pharmaceutically acceptable salts with a general formula I or II.

The invention further relates to the use of the compounds with general formula I or II as active ingredients for the preparation of medicaments.

Compounds with the general formula I or II are the inhibitors of the enzyme butyrylcholinesterase and are used for the treatment of symptoms of Alzheimer's disease, multiple sclerosis, all forms of dementias and cognitive disorders related to decreased cholinergic neurotransmission.

The invention is related to parenteral, per oral or other pharmaceutically acceptable forms containing the compounds with the general formula I or II.

Beside active pharmaceutical ingredient, the pharmaceutical composition can contain excipients suitable for the intended route of administration.

Pharmaceutical compositions are prepared using standard procedures.

Pharmaceutical compositions can be prepared in the way that ensures the sustained release of the active pharmaceutical ingredient.

The dose, frequency and way of use are dependent from several factors, which are further dependent also from the active pharmaceutical ingredient used, its pharmacokinetic properties and patient's condition.

Compounds with general formula I can be prepared using modified synthetic procedures described in the literature (Košak U. et al. *Tetrahedron Lett.* 2014, 55, 2037-2039; Brus B. et al. *J. Med Chem.* 2014, 57, 8167-8179). Compounds with the general formula II can be prepared using procedures described in the chapter Synthesis of the compounds with the general formula II.

The invention is clarified, though not limited by the following examples.

EXAMPLES

Biological Evaluation
I. Enzyme Assay for the Determination of BChE Inhibitors Potency
1. Principle
Ellman's method was used to evaluate the inhibitory activities of the synthesized compounds against the cholinesterases. (Ellman G. L. et al. *Biochem. Pharmacol.* 1961, 7, 88-95) Employing this reaction the concentration of thiol groups are determined using Ellman's reagent (5,5'-dithiobis (2-nitrobenzoic acid), DTNB). As a substrate butyrylthiocholine (BTC) and acetylthiocholine (ATC) iodides were used for BChE and AChE, respectively. Enzyme cleaves the corresponding substrate to thiocholine, which further reacts with DTNB and forms the yellow colored product, 5-thio-2-nitrobenzoate anion. The reaction was monitored using a 96-well microtiter plate and a 96-well microplate reader (Synergy™ H4, BioTek Instruments, Inc., USA) as change in absorbance at 412 nm. For the reference sample, 1% dimethylsulfoxide (DMSO) replaced the inhibitor's solution.

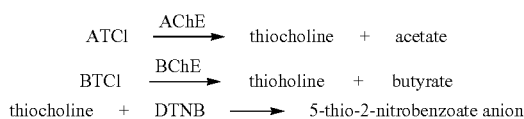

Potency of the inhibitor is expressed as a residual activity (RA) of the enzyme at the employed inhibitor's concentration, half maximal inhibitory concentration (IC$_{50}$ value) and as an inhibition constant (K$_i$).

2. Reagents

Ezymes:

The enzyme reactions were carried out using murine acetylcholinesterase (mAChE) and human recombinant butyrylcholinesterase (huBChE). From the lyophilised powders of both enzymes, the solutions were obtained by dissolution of the powders in 10 mM MES buffer (pH 6.5) to reach the concentration of 4 mg/mL. The concentrated enzyme solution was diluted prior use in 100 mM phosphate buffer (pH 8.0) to reach the activity of the enzyme in the assay of approximately 500 mAu per minute.

Substrates, ATCI and BTCI:

ATCI in BTCI solutions were prepared in 100 mM phosphate buffer (pH 8.0) to reach the final concentration in the assay of 500 μM.

Ellman's Reagent, DTNB:

DTNB solution was prepared in 100 mM phosphate buffer (pH 8.0) to reach the final concentration in the assay of 333 μM.

Investigated Compounds:

Stock solutions of compounds were prepared in DMSO in a concentration of 10 mM. For the IC$_{50}$ determination, the stock solutions were further diluted in DMSO to reach the range of inhibition from 5-95% in the final assay.

3. Procedure

Enzyme solutions were prepared by dilution of the concentrated stocks in the 100 mM phosphate buffer (pH 8.0). The reactions were carried out in microtiter plates in a final volume of 300 μL containing phosphate buffer, 333 μM DTNB, $5\times10^{-4}$ M BTCI/ATCI and $1\times10^{-9}$ M or $5\times10^{-11}$ M of huBChE or mAChE, respectively. Enzyme reaction was started with the addition of the substrate. The DMSO concentration in the test solution was always 1%. The formation of yellow colored product of the reaction of DTNB with thiocholines was monitored for 1 minute as a change in absorbance at 412 nm using the microtiter plate reader (Synergy™ H4, BioTek Instruments, Inc., USA). For the determination of blank (b) the phosphate buffer replaced the enzyme solution. Initial velocity of the enzyme reaction (v$_o$) was determined from the linear curve of the enzyme reaction product formation, where each measurement was performed in triplicate. For the initial screening of inhibition ability, 1 mM concentration of the investigated compounds was used. Compounds were pipetted in the corresponding wells to reach the final concentration of 10 μM. Tested compound and the enzyme solution were first preincubated for 300s, followed by the substrate addition, which triggered the enzyme reaction. The initial velocity in presence of the inhibitor was further calculated (v$_i$). The inhibition capability was expressed as residual activity (RA=(v$_i$-b)/(v$_o$-b)).

For the IC$_{50}$ value determination, 8 different concentrations of the investigated compounds were used, which resulted in the decrease of the enzyme reaction from 5% do 90%. IC$_{50}$ values were determined by plotting the RA versus the concentration of the investigated compound. Experimental data were fitted using the following equation (1):

$$Y = \text{Min} + (\text{Max}-\text{Min})/(1+10^{((\text{Log } IC_{50}-X)\times \text{Hill Slope})}) \quad (1),$$

Where X is a common logarithm of the concentration of the inhibitor and Y is the residual activity. For solving the equation Gnuplot software and an in-house python script were used. For the determination of the inhibition constant full progress curves of the product formation in presence and absence of investigated compounds were monitored. The curves were submitted in the ENZO web-application, which allows solving of numerical equations. (Bevc et al., *PLoS One* 2011, 6, e22265)

Results of Biological Evaluation

TABLE 1

Inhibitory activity of compounds with general formula (I).

(I)

[Structure: piperidine with X substituent on N, and CH$_2$-N(Y)-C(=O)-Z side chain at 3-position]

| X | Y | Z | IC$_{50}$ ± STD (nM) huBChE | % inhibition ± STD at 10 μM inhibitor mAChE |
|---|---|---|---|---|
| [methyl-indane] | —CH$_2$—CH$_2$—NMe$_2$ | [methyl-naphthyl] | 1.03 ± 0.04 | 17.4 ± 3.7 |

TABLE 1-continued

Inhibitory activity of compounds with general formula (I).

(I)

[Structure of general formula (I): piperidine with N-X, 3-position CH2-N(Y)-C(=O)-Z]

| X | Y | Z | IC$_{50}$ ± STD (nM) huBChE | % inhibition ± STD at 10 μM inhibitor mAChE |
|---|---|---|---|---|
| [2-methyl-indane] | | —CH$_2$—CH$_2$—NMe$_2$ | 9.5 ± 0.001 | n.d. |
| [2-methyl-indane] | | [3-methyl-2H-chromen-2-one] | 13.18 ± 0.61 | n.d. |
| [2-methyl-indane] | | [7-methyl-8-hydroxyquinoline] | | |

STD = standard deviation
n.d. = not done
huBChE = human butyrycholinesterase
mAChE = murine acetylcholinesterase TABLE 2
Inhibitory activity of compounds with general formula (I).
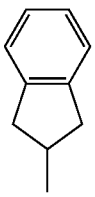
(II)
| Disub-stitucijana piperidinu | W | V | Q | IC$_{50}$ ± STD (μM) or % inhibition at 10 μM huBChE | IC$_{50}$ ± STD (μM) or % inhibition at 10 μM mAChE |
|---|---|---|---|---|---|
| 1,3- | 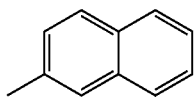 | —CH$_2$—CH$_2$—OMe | 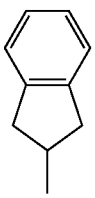 | 0.053 ± 0.004 μM | 72 ± 0.86% |
| 1,3- | 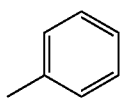 | —CH$_2$—CH$_2$—OMe | 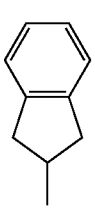 | 0.343 ± 0.005 μM | n.i. |
| 1,3- | 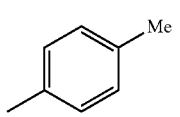 | —CH$_2$—CH$_2$—OMe | 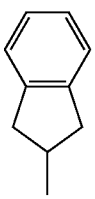 Me | 0.279 ± 0.008 μM | n.i. |
| 1,3- | 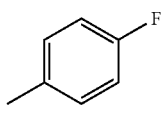 | —CH$_2$—CH$_2$—OMe | 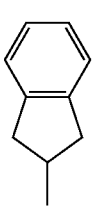 F | 0.887 ± 0.08 μM | n.i. |
| 1,3- | 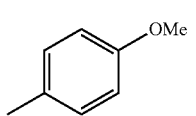 | —CH$_2$—CH$_2$—OMe | OMe | 0.482 ± 0.066 μM | n.i. |

TABLE 2-continued
Inhibitory activity of compounds with general formula (I).
(II)
| Disub-stitucijana piperidinu | W | V | Q | IC$_{50}$ ± STD (μM) or % inhibition at 10 μM huBChE | IC$_{50}$ ± STD (μM) or % inhibition at 10 μM mAChE |
|---|---|---|---|---|---|
| 1,3- | 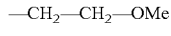 | —CH$_2$—CH$_2$—OMe | 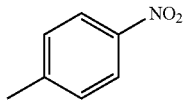 p-NO$_2$ | 3.466 ± 0.052 μM | n.i. |
| 1,3- |  | —CH$_2$—CH$_2$—OMe | 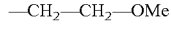 p-NH$_2$ | 0.314 ± 0.036 μM | n.i. |
| 1,3- | 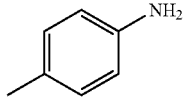 | —CH$_2$—CH$_2$—OMe |  p-NHAc | 0.321 ± 0.035 μM | n.i. |
| 1,3- | 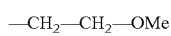 | —CH$_2$—CH$_2$—OMe | 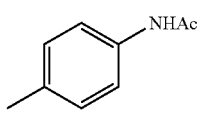 m-NO$_2$ | 3.611 ± 0.528 μM | 68 ± 4.42% |
| 1,3- |  | —CH$_2$—CH$_2$—OMe | 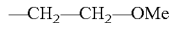 m-NH$_2$ | 0.197 ± 0.008 μM | n.i. |

TABLE 2-continued
Inhibitory activity of compounds with general formula (I).
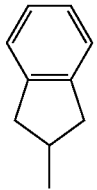
| Disub-stitucijana piperidinu | W | V | Q | IC$_{50}$ ± STD (µM) or % inhibition at 10 µM huBChE | IC$_{50}$ ± STD (µM) or % inhibition at 10 µM mAChE |
|---|---|---|---|---|---|
| 1,3- | 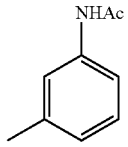 | —CH$_2$—CH$_2$—OMe |  NHAc | 8.207 ± 0.601 µM | n.i. |
| 1,3- | 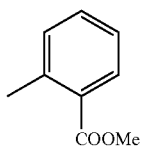 | —CH$_2$—CH$_2$—OMe |  COOMe | 0.359 ± 0.018 µM | n.i. |
| 1,3- | 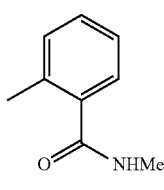 | —CH$_2$—CH$_2$—OMe | 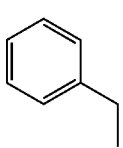 NHMe | 3.225 ± 0.492 µM | n.i. |
| 1,3- | 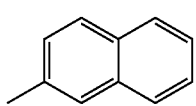 | —CH$_2$—CH$_2$—OMe | 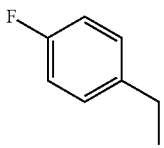 | 0.0049 ± 0.0003 µM | n.i. |
| 1,3- | 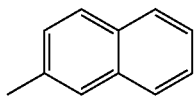 | —CH$_2$—CH$_2$—OMe | 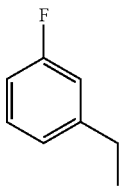 | 0.231 ± 0.006 µM | n.i. |
| 1,3- | 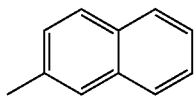 | —CH$_2$—CH$_2$—OMe |  | 0.0491 ± 0.0012 µM | n.i. |

TABLE 2-continued
Inhibitory activity of compounds with general formula (I).
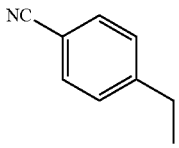
(II)
| Disub-stitucijana piperidinu | W | V | Q | IC$_{50}$ ± STD (μM) or % inhibition at 10 μM huBChE | IC$_{50}$ ± STD (μM) or % inhibition at 10 μM mAChE |
|---|---|---|---|---|---|
| 1,3- | 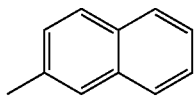 | —CH$_2$—CH$_2$—OMe | 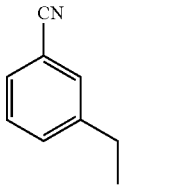 | 1.464 ± 0.115 μM | n.i. |
| 1,3- | 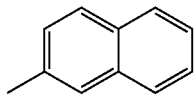 | —CH$_2$—CH$_2$—OMe | 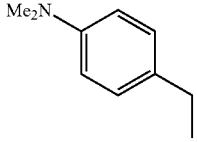 | 0.338 ± 0.008 μM | n.i. |
| 1,3- | 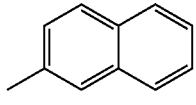 | —CH$_2$—CH$_2$—OMe | 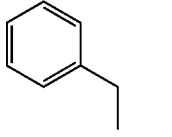 | 0.311 ± 0.022 μM | n.i. |
| 1,3- | 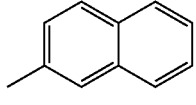 | —H | 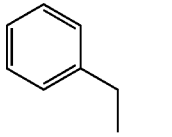 | 0.0569 ± 0.0098 μM | n.i. |
| 1,3- | 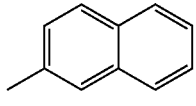 | —Me | 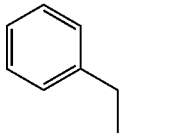 | 0.0250 ± 0.0038 μM | n.i. |
| 1,3- | 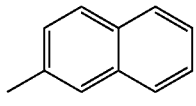 | —Et | 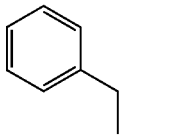 | 0.0380 ± 0.0026 μM | n.i. |
| 1,3- | 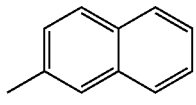 | —n-Pr | | 0.0428 ± 0.0064 μM | n.i. |

TABLE 2-continued
Inhibitory activity of compounds with general formula (I).
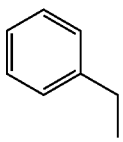
(II)
| Disub-stitucijana piperidinu | W | V | Q | IC$_{50}$ ± STD (μM) or % inhibition at 10 μM huBChE | IC$_{50}$ ± STD (μM) or % inhibition at 10 μM mAChE |
|---|---|---|---|---|---|
| 1,3- | 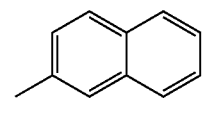 | —n-Bu | 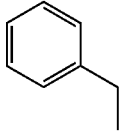 | 0.0355 ± 0.0044 μM | n.i. |
| 1,3- | 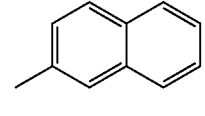 | —CH$_2$—CH$_2$—CH$_2$—OMe | 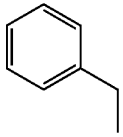 | 0.0144 ± 0.0008 μM | n.i. |
| 1,4- | 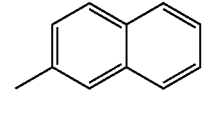 | —CH$_2$—CH$_2$—OMe | 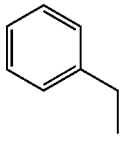 | 0.0394 ± 0.0028 μM | n.i. |
| 1,4- | 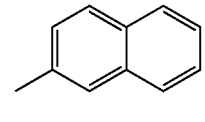 | —CH$_2$—CH$_2$—CH$_2$—OMe | 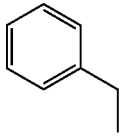 | 0.0193 ± 0.0037 μM | n.i. |
| 1,4- | 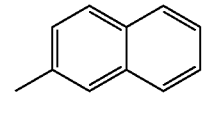 | —H | 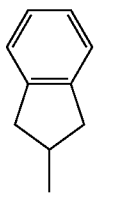 | 0.195 ± 0.017 μM | 1.78 ± 0.085 μM |
| 1,4- | 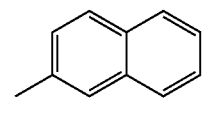 | —CH$_2$—CH$_2$—OMe |  | 0.0525 ± 0.0020 μM | n.i. |

TABLE 2-continued

Inhibitory activity of compounds with general formula (I).

(II) General structure: 1-W-piperidine with CH2-N(V)-SO2-Q substituent

| Disub-stitucijana piperidinu | W | V | Q | IC$_{50}$ ± STD (μM) or % inhibition at 10 μM huBChE | IC$_{50}$ ± STD (μM) or % inhibition at 10 μM mAChE |
|---|---|---|---|---|---|
| 1,4- | 2,3-dihydro-1H-inden-2-ylmethyl | —CH$_2$—CH$_2$—CH$_2$—OMe | naphthalen-2-yl | 0.0712 ± 0.0019 μM | n.i. |
| 1,3 | 3-methylbenzyl | —H | naphthalen-2-yl | 0.287 ± 0.022 μM | 57 ± 3.55% |
| 1,3- | 4-fluorobenzyl | —H | naphthalen-2-yl | 0.583 ± 0.043 μM | 75 ± 4.19% |
| 1,3- | (2-methylthiazol-4-yl)methyl | —H | naphthalen-2-yl | 0.366 ± 0.031 μM | 71 ± 3.68% |
| 1,3- | 2-chloro-4-fluorobenzyl | —H | naphthalen-2-yl | 0.347 ± 0.060 μM | 73 ± 3.60% |
| 1,3- | pyridin-4-ylmethyl | —H | naphthalen-2-yl | 1.673 ± 0.256 μM | n.i. |

TABLE 2-continued

Inhibitory activity of compounds with general formula (I).

(II) Structure: 1-W-piperidine with CH2-N(V)-SO2-Q substituent

| Disubstitucijana piperidinu | W | V | Q | IC$_{50}$ ± STD (μM) or % inhibition at 10 μM huBChE | IC$_{50}$ ± STD (μM) or % inhibition at 10 μM mAChE |
|---|---|---|---|---|---|
| 1,3- | 4-NC-C$_6$H$_4$-CH$_2$CH$_2$- | —H | naphthalen-2-yl | 2.093 ± 0.328 μM | n.i. |
| 1,3- | benzothiazol-2-yl-CH$_2$- | —H | naphthalen-2-yl | 51% | n.i. |
| 1,3- | 4-F-C$_6$H$_4$-CH$_2$CH$_2$- | —Me | naphthalen-2-yl | 0.427 ± 0.044 μM | n.i. |
| 1,3- | C$_6$H$_5$-CH$_2$CH$_2$- | —CH$_2$—CH$_2$—OMe | naphthalen-1-yl | 0.059 ± 0.0054 μM | n.i. |
| 1,3- | C$_6$H$_5$-CH$_2$CH$_2$- | —CH$_2$—CH$_2$—OMe | 7-methoxynaphthalen-2-yl | 0.156 ± 0.033 μM | n.i. |
| 1,3- | C$_6$H$_5$-CH$_2$CH$_2$- | —CH$_2$—CH$_2$—CH$_2$—OMe | 7-(cyanomethoxy)naphthalen-2-yl | 0.113 ± 0.008 μM | n.i. |

STD = standard deviation
n.i. = no inhibiton
huBChE = human butyrycholinesterase
mAChE = murine acetylcholinesterase

Synthesis of Compounds with General Formula (I)

Example 1: Synthesis of (±)-N-((1-(2,3-dihydro-1H-inden-2-yl)piperidin-3-yl)methyl)-N-(2-(dimethylamino)ethyl)-2-naphthamide

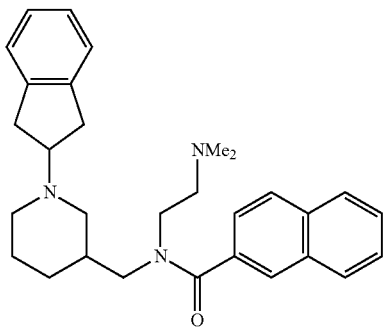 [SMILES: CN(C)CCN(CC1CCCN(C2Cc3ccccc3C2)C1)C(=O)c1ccc2ccccc2c1]

Step 1: Synthesis of (±)-1-benzoylpiperidine-3-carboxylic acid

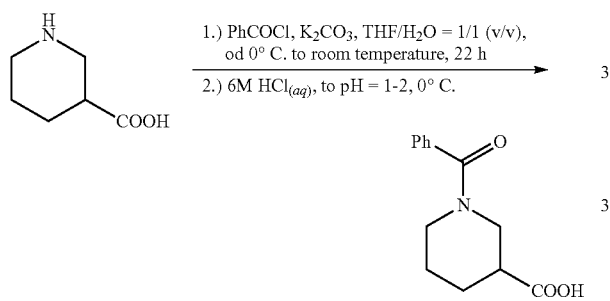

To a 250-mL round-bottomed flask equipped with a stirring bar, nipecotic acid (9.946 g, 77.007 mmol, 1.0 equiv) was added. THF (80 mL), H$_2$O (80 mL) and K$_2$CO$_3$ (53.214 g, 385.023 mmol, 5.0 equiv) were added, and the mixture was cooled to 0° C. A solution of benzoyl chloride (8.931 mL, 77.007 mmol, 1.0 equiv) in THF (35 mL) was added drop-wise. The reaction mixture was allowed to warm to r.t. and then stirred for 22 h. The reaction mixture was transferred into a 500-mL separating funnel and washed with EtOAc (3×150 mL). The aqueous phase was cooled to 0° C. and adjusted to pH 1-2 with 6 M aq HCl. The white precipitate was collected in a Büchner funnel under suction filtration, and then dried in vacuo at room temperature in the presence of NaOH, P$_2$O$_5$ and silica gel to constant mass to produce 17.028 g of (±)-1-benzoylpiperidine-3-carboxylic acid. This product was used in the next step without further purification.

Product appearance: white solid
Yield: 95%
Melting point: 171-175° C.
TLC: 0.53 (MeCN-MeOH—H$_2$O=3/1/1, v/v/v)
IR (ATR): 2865, 2563, 1709, 1584, 1564, 1464, 1277, 1212, 929, 861, 791, 729, 632, 572 cm$^{-1}$.

$^1$H NMR (400 MHz, DMSO-d6): δ=1.45-1.69 (3H, m), 1.96-2.00 (1H, m), 2.42-2.46 (1H, m), 3.00-3.17 (2H, m), 3.45-3.63 (1H, m), 4.13-4.43 (1H, m), 7.37-7.52 (5H, m), 12.44 (1H, bs).

$^{13}$C NMR (100 MHz, DMSO-d6): δ=23.63, 24.40, 26.79, 40.63, 41.54, 43.41, 47.29, 48.72, 48.72, 126.64, 128.33, 129.32, 136.24, 169.14, 174.24.

HRMS (ESI$^+$): m/z calculated for C$_{13}$H$_{16}$NO$_3$: 234.1130; found: 231.1129.

CHN analysis: calculated for C$_{13}$H$_{15}$NO$_3$: C, 66.94; H, 6.48; N, 6.00. Found: C, 67.15; H, 6.74; 6.16.

Step 2: Synthesis of (±)-1-benzoyl-N-(2-(dimethylamino)ethyl)piperidine-3-carboxamide

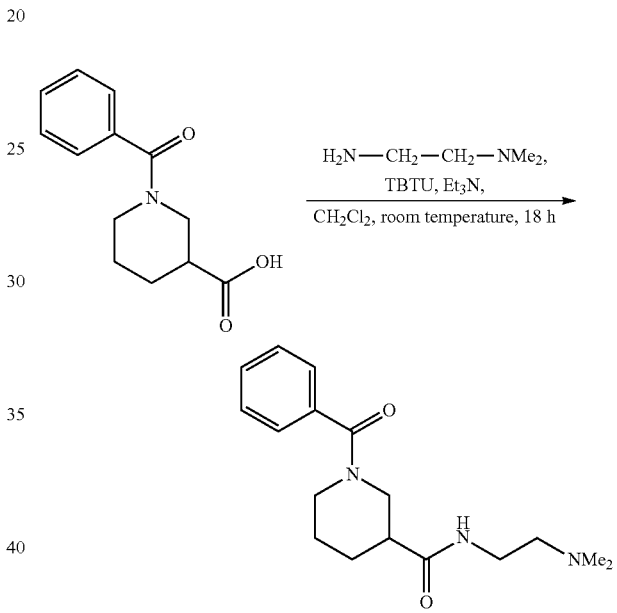

To a 500-mL round-bottomed flask equipped with a stirring bar, (±)-1-benzoylpiperidine-3-carboxylic acid (17.000 g, 72.876 mmol) and CH$_2$Cl$_2$ (350 mL) were added. Et$_3$N (20.205 mL, 145.754 mmol) was added drop-wise, followed by TBTU (23.400 g, 72.876 mmol). After 30 min, N,N-dimethylethylenediamine (15.900 mL, 145.754 mmol) was added dropwise, and the reaction mixture was stirred for 18 h. The reaction mixture was transferred into a 1000-mL separating funnel and washed with sat. aq NaHCO$_3$ (2×150 mL), H$_2$O (2×150 mL) followed by sat. brine solution (150 mL), and dried over anhyd Na$_2$SO$_4$ and evaporated, to produce 27,190 g of crude (±)-1-benzoyl-N-(2-(dimethylamino)ethyl)piperidine-3-carboxamide. This product was used in the next step without further purification.

Product appearance: golden-yellow oil
TLC: R$_f$=0.19 (CH$_2$Cl$_2$-MeOH=9:1, v/v)
HRMS (ESI+): m/z calculated for C$_{17}$H$_{26}$N$_3$O$_2$: 304.2025; found: 304.2018.

Step 3: Synthesis of (±)-N$^1$-((1-benzylpiperidin-3-yl)methyl)-N$^2$,N$^2$-dimethylethane-1,2-diamine

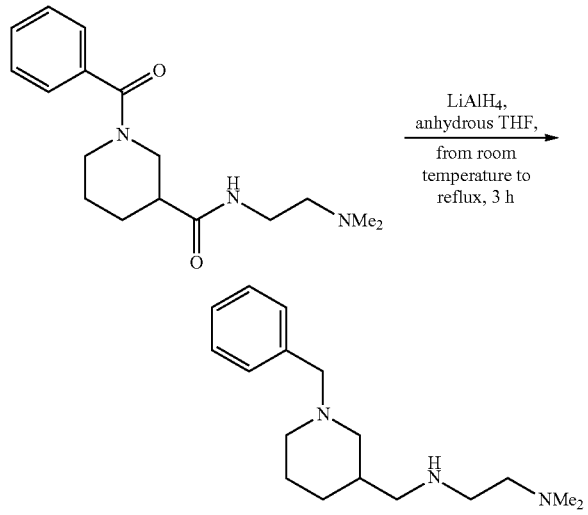

To a 500-mL tree-neck round-bottomed flask equipped with a stirring bar and a reflux condenser, LiAlH$_4$ (4.378 g, 115.359 mmol) was added under an argon atmosphere. Anhydrous THF (ca. 120 mL) was added with a double-tipped needle. A solution of crude (±)-1-benzoyl-N-(2-(dimethylamino)ethyl)piperidine-3-carboxamide (7.000 g, 23.072 mmol) in anhydrous THF (ca. 60 mL) was added with a double-tipped needle, and the reaction mixture was refluxed for 3 h. The mixture was then cooled to 0° C. and the excess hydride was decomposed by drop-wise addition of H$_2$O (4.378 mL) followed by 15% aq NaOH (4.378 mL) and then H$_2$O (13.134 mL). After vigorous stirring for 1 h at r.t., the mixture was filtered under suction and the white precipitate was washed thoroughly with THF (5×60 mL). The combined filtrates were evaporated to produce 4.239 g of (±)-N$^1$-((1-benzylpiperidin-3-yl)methyl)-N$^2$,N$^2$-dimethylethane-1,2-diamine. This product was used in the next step without further purification.

Product appearance: colorless oil

TLC: R$_f$=0.04 (CH$_2$Cl$_2$-MeOH=9:1, v/v+0.3% Et$_3$N)

HRMS (ESI+): m/z calculated for C$_{17}$H$_{30}$N$_3$: 276.2440; found: 276.2439.

Step 4: Synthesis of (±)-tert-butyl ((1-benzylpiperidin-3-yl)methyl)(2-(dimethylamino)ethyl)carbamate

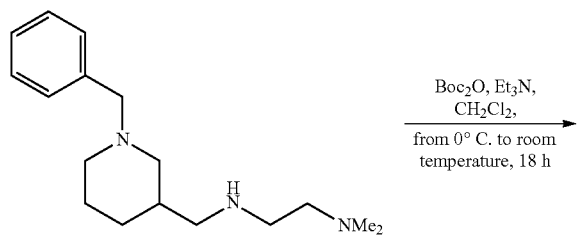

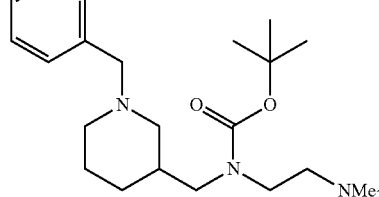

CH$_2$Cl$_2$ (150 mL) and a stirring bar were added to crude (±)-N$^1$-((1-benzylpiperidin-3-yl)methyl)-N$^2$,N$^2$-dimethylethane-1,2-diamine (4.239 g, 15.390 mmol) in a 250-mL round-bottomed flask. Et$_3$N (2.133 mL, 15.390 mmol) was added drop-wise, and the reaction mixture was cooled to 0° C. A solution of Boc$_2$O (3.359 g, 15.390 mmol) in CH$_2$Cl$_2$ (20 mL) was added drop-wise, and the reaction mixture was allowed to warm to r.t. and then stirred for 18 h. The reaction mixture was transferred into a 500-mL separating funnel and washed with H$_2$O (150 mL), sat. aq NaHCO$_3$ (150 mL), dried over anhyd Na$_2$SO$_4$, and evaporated. The residue was purified by flash column chromatography using CH$_2$Cl$_2$-MeOH (9:1, v/v) as the eluent to produce 3.190 g of (±)-tert-butyl ((1-benzylpiperidin-3-yl)methyl)(2-(dimethylamino)ethyl)carbamate.

Product appearance: slightly golden-yellow oil

Yield: 37% (from (±)-1-benzoylpiperidine-3-carboxylic acid)

TLC: R$_f$=0.42 (CH$_2$Cl$_2$-MeOH=9:1, v/v)

IR (ATR): 2972, 2933, 2766, 1690, 1455, 1416, 1365, 1247, 1156, 1096, 1068, 1025, 886, 863, 773, 739, 698 cm$^{-1}$ $^1$H NMR (400 MHz, CDCl$_3$): δ=0.85-0.97 (1H, m), 1.38 (9H, s), 1.47-1.54 (1H, m), 1.59-1.66 (3H, m), 1.81-1.94 (2H, m), 2.20 (3H, s), 2.21 (3H, s), 2.31 (1H, t, J=7.4 Hz), 2.38 (1H, t, J=7.0 Hz), 2.72 (2H, bs), 3.02-3.06 (2H, m), 3.11-3.27 (2H, m), 3.45 (2H, s), 7.17-7.26 (5H, m).

$^{13}$C NMR (100 MHz, CDCl$_3$): δ=24.81, 28.32, 28.52, 35.61, 36.03, 45.43, 45.57, 45.67, 50.84, 51.25, 53.93, 54.13, 56.81, 57.51, 57.70, 58.06, 63.50, 79.20, 79.28, 126.82, 126.86, 128.06, 129.06, 129.13, 138.09, 138.20, 155.55.

HRMS (ESI+): m/z calculated for C$_{22}$H$_{38}$N$_3$O$_2$: 376.2964; found: 376.2972.

Step 5: Synthesis of (±)-tert-butyl (2-(dimethylamino)ethyl)(piperidin-3-ylmethyl)carbamate

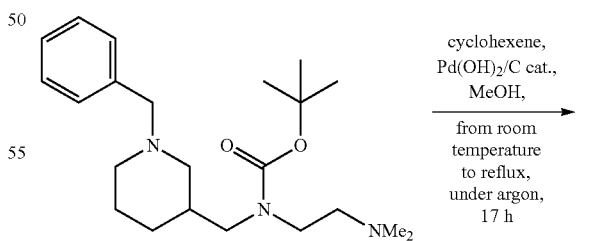

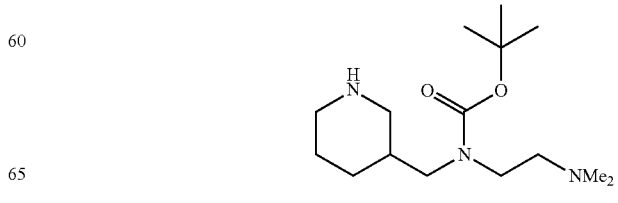

To a 250-mL round-bottomed flask with a stirring bar, (±)-tert-butyl ((1-benzylpiperidin-3-yl)methyl)(2-(dimethylamino)ethyl)carbamate (3.190 g, 8.494 mmol) and MeOH (70 mL) were added at room temperature. The resulting solution was stirred and agitated with a stream of argon for 15 min. Pd(OH)$_2$ on carbon (20 wt. %) (0.320 g, 10% mass of (±)-tert-butyl ((1-benzylpiperidin-3-yl)methyl)(2-(dimethylamino)ethyl)carbamate) was added, followed by cyclohexene (8.150 mL, 84.942 mmol). The resulting suspension was refluxed under an atmosphere of argon for 15 h, then filtered through a pad of Celite, and evaporated, to produce 2.410 g of crude (±)-tert-butyl (2-(dimethylamino)ethyl)(piperidin-3-ylmethyl)carbamate. This product was used in the next step without further purification.

Product appearance: slightly yellow oil
Yield: 97%
TLC: $R_f$=0.09 (CH$_2$Cl$_2$-MeOH=9:1, v/v+0.3% Et$_3$N)
IR (ATR): 3368, 2978, 1671, 1560, 1477, 1405, 1368, 1313, 1251, 1159, 1042, 1015, 649 cm$^{-1}$
$^1$H NMR (400 MHz, CDCl$_3$): δ=0.80-0.94 (1H, m), 1.02-1.14 (1H, m), 1.44 (9H, s), 1.49-1.75 (3H, m), 1.81-1.91 (1H, m), 2.23 (6H, s), 2.36-2.44 (2H, m), 2.53-2.62 (0.5H, m), 2.72-2.76 (0.5H, m), 2.84-3.10 (4H, m), 3.16-3.31 (2H, m)
HRMS (ESI+): m/z calculated for C$_{15}$H$_{32}$N$_3$O$_2$: 286.2495; found: 286.2487.

Step 6: Synthesis of (±)-tert-butyl ((1-(2,3-dihydro-1H-inden-2-yl)piperidin-3-yl)methyl)(2-(dimethylamino)ethyl)carbamate

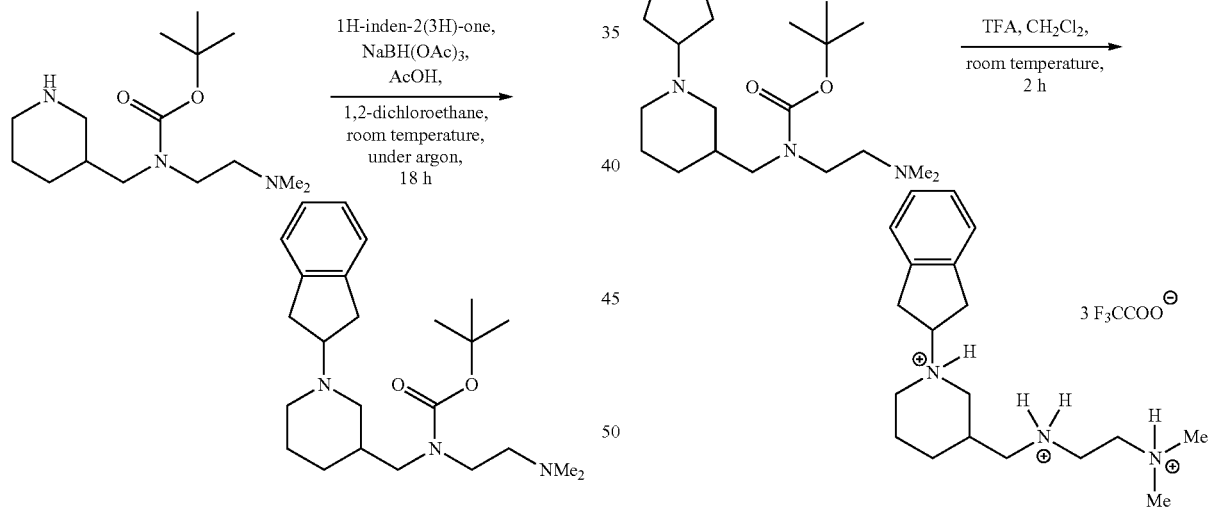

To a 100-mL round-bottomed flask with a stirring bar, (±)-tert-butyl (2-(dimethylamino)ethyl)(piperidin-3-ylmethyl)carbamate (1.920 g, 6.727 mmol) and 1,2-dichloroethane (50 mL) were added at room temperature. The resulting solution was stirred and agitated with a stream of argon for 15 min. NaBH(OAc)$_3$ (4.277 g, 20.181 mmol), 1H-inden-2(3H)-one (0.889 g, 6.727 mmol) and AcOH (0.577 mL, 10.091 mmol) were added, and the resulting suspension was stirred under an atmosphere of argon for 18 h. The reaction mixture was opened to the air and quenched with saturated aqueous NaHCO$_3$ solution (50 mL). The mixture was transferred into a 250-mL separating funnel, and CH$_2$Cl$_2$ (50 mL) was added. The separating funnel was shaken vigorously and the organic phase was separated, dried over anhydrous Na$_2$SO$_4$, and evaporated. The residue was purified by flash column chromatography using CH$_2$Cl$_2$/MeOH (9:1, v/v) as the eluent, to produce 1.870 g (±)-tert-butyl ((1-(2,3-dihydro-1H-inden-2-yl)piperidin-3-yl)methyl)(2-(dimethylamino)ethyl)carbamate.

Product appearance: slightly golden-yellow oil
Yield: 69% (from (±)-tert-butyl ((1-benzylpiperidin-3-yl)methyl)(2-(dimethylamino)ethyl)carbamate)
TLC: $R_f$=0.11 (CH$_2$Cl$_2$-MeOH=9:1, v/v)
IR (ATR): 2934, 2766, 1690, 1461, 1416, 1390, 1365, 1249, 1156, 1099, 1023, 937, 888, 863, 771, 742 cm$^{-1}$
$^1$H NMR (400 MHz, CDCl$_3$): δ=0.87-1.01 (1H, m), 1.44 (9H, s), 1.60-1.83 (4H, m), 1.92-1.97 (2H, m), 2.24 (6H, s), 2.38-2.46 (2H, m), 2.86-2.96 (4H, m), 3.01-3.15 (5H, m), 3.24 (1H, t, J=7.2 Hz), 3.30 (1H, t, J=7.4 Hz), 7.08-7.14 (4H, m)
$^{13}$C NMR (100 MHz, CDCl$_3$): δ=24.80, 24.89, 28.33, 28.68, 35.69, 36.02, 36.81, 37.02, 45.43, 45.55, 45.64, 50.88, 51.45, 52.11, 56.16, 56.43, 56.82, 57.52, 67.19, 79.33, 124.25, 126.27, 141.35, 141.39, 155.51, 155.62.
HRMS (ESI+): m/z calculated for C$_{14}$H$_{40}$N$_3$O$_2$: 402.3121; found: 402.3115.

Step 7: Synthesis of (±)-N$^1$-((1-(2,3-dihydro-1H-inden-2-yl)piperidin-3-yl)methyl)-N$^2$,N$^2$-dimethylethane-1,2-diamine tri(2,2,2-trifluoroacetate)

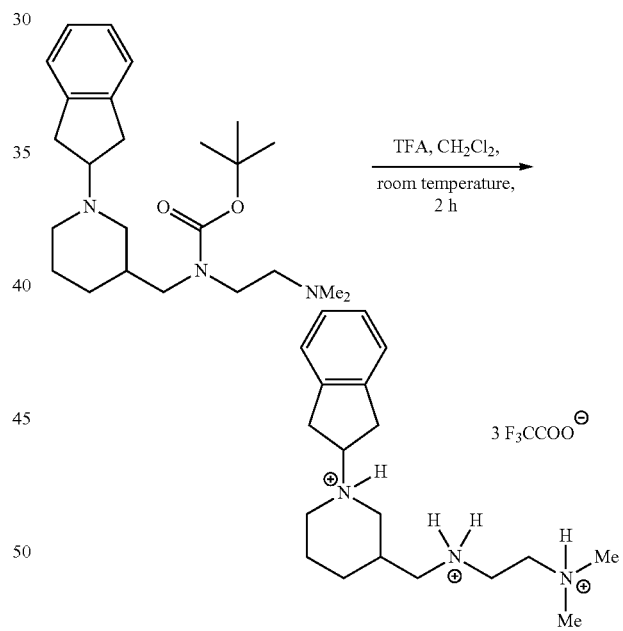

To a 50-mL round-bottomed flask equipped with a stirring bar, (±)-tert-butyl ((1-(2,3-dihydro-1H-inden-2-yl)piperidin-3-yl)methyl)(2-(dimethylamino)ethyl)carbamate (1,870 g, 4,656 mmol) and CH$_2$Cl$_2$ (20 mL) were added at room temperature. The resulting solution was stirred and TFA (16.045 mL, 209.542 mmol) was added drop-wise. After 2 h, the reaction mixture was evaporated. The residue was co-evaporated with CH$_2$Cl$_2$ (2×30 mL), followed by n-hexane (2×30 mL). Et$_2$O (30 mL) was added to the oily residue, and the flask was placed in an ultrasonic bath for 15 min. During this time, the oily residue transformed into a white solid. The flask was removed from the ultrasonic bath and the precipitate was allowed to settle to the bottom of the flask. The supernatant was removed, Et$_2$O (30 mL) was added, and the flask was placed back in the ultrasonic bath for 1 min. The flask was removed from the ultrasonic bath and the precipitate was allowed to settle to the bottom of the flask. The supernatant was removed, Et$_2$O (30 mL) was added again, and this procedure was repeated two more times. After the final supernatant was removed, the solid residue was dried at reduced pressure to produce 3.020 g of crude (±)-N$^1$-((1-(2,3-dihydro-1H-inden-2-yl)piperidin-3-yl)methyl)-N$^2$,N$^2$-dimethylethane-1,2-diamine tri(2,2,2-trifluoroacetate). This product was used in the next step without further purification.

Product appearance: white solid
Yield: 99%
TLC: R$_f$=0.08 (CH$_2$Cl$_2$-MeOH=9:1, v/v)
IR (ATR): 2674, 1664, 1476, 1418, 1174, 1118, 1001, 973, 830, 798, 776, 748, 719 cm$^{-1}$
$^1$H NMR (400 MHz, MeOD): δ=1.36-1.50 (1H, m), 1.84-1.94 (1H, m), 2.03-2.11 (2H, m), 2.39-2.49 (1H, m), 2.87-3.03 (8H, m), 3.15 (2H, bd, J=6.4 Hz), 3.27 (2H, dd, J=16.0, 8.0 Hz), 3.41-3.49 (2H, m), 3.56-3.65 (5H, m), 3.87 (1H, bd, J=11.6 Hz), 4.10 (1H, p, J=8.2 Hz), 7.22-7.29 (4H, m), NH exchanged
HRMS (ESI+): m/z calculated for C$_{19}$H$_{32}$N$_3$: 302.2596; found: 302.2591.

Step 8: Synthesis of (±)-N-((1-(2,3-dihydro-1H-inden-2-yl)piperidin-3-yl)methyl)-N-(2-(dimethylamino)ethyl)-2-naphthamide

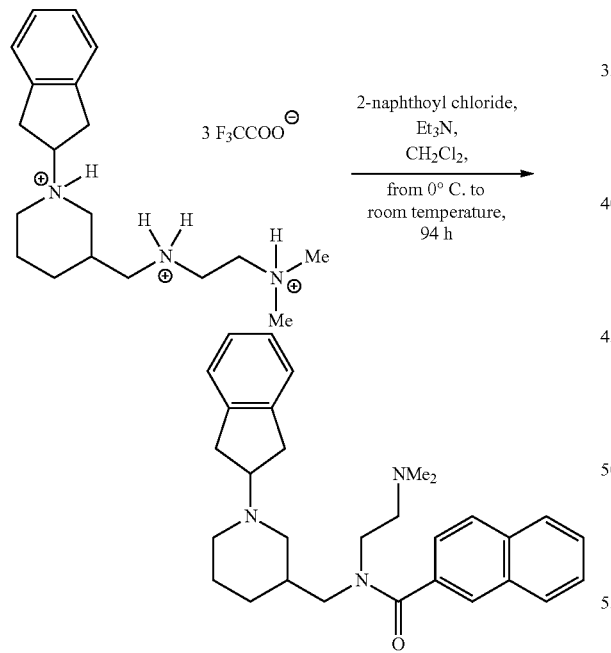

To a 250-mL round-bottomed flask with a stirring bar, (±)-N$^1$-((1-(2,3-dihydro-1H-inden-2-yl)piperidin-3-yl)methyl)-N$^2$,N$^2$-dimethylethane-1,2-diamine tri(2,2,2-trifluoroacetate) (2.418 g, 3.757 mmol) and CH$_2$Cl$_2$ (150 mL) were added. The resulting suspension reaction mixture was stirred and cooled to 0° C. Et$_3$N (2.095 mL, 15.028 mmol) was added drop-wise, followed by 2-naphtoyl chloride (0.716 g, 3.757 mmol) and the reaction mixture was allowed to warm to r.t. and then stirred for 94 h. The reaction mixture was transferred into a 500-mL separating funnel and washed with H$_2$O (150 mL), sat. aq NaHCO$_3$ (150 mL), dried over anhyd Na$_2$SO$_4$, and evaporated. The residue was purified by flash column chromatography using CH$_2$Cl$_2$-MeOH-Et$_3$N (120:10:1, v/v/v) as the eluent to produce 1.172 g of (±)-N-((1-(2,3-dihydro-1H-inden-2-yl)piperidin-3-yl)methyl)-N-(2-(dimethylamino)ethyl)-2-naphthamide.

Product appearance: golden-brown oil
Yield: 68%
TLC: R$_f$=0.14 (CH$_2$Cl$_2$-MeOH-Et$_3$N=150:10:1, v/v/v)
$^1$H NMR (400 MHz, DMSO-d6, 80° C.): δ=0.95 (1H, bs), 1.43-1.51 (1H, m), 1.59-1.67 (2H, m), 1.81 (1H, bs), 1.98-2.09 (7H, m), 2.70-2.83 (4H, m), 2.96-3.21 (6H, m), 3.35-3.45 (4H, m), 7.09-7.20 (4H, m), 7.41-7.43 (1H, m), 7.55-7.59 (2H, m), 7.87 (1H, s), 7.94-7.98 (3H, m).
HRMS (ESI+): m/z calculated for C$_{31}$H$_{40}$N$_3$O 470.3171; found: 470.3180.

Example 2: Synthesis of (±)-N-((1-(2,3-dihydro-1H-inden-2-yl)piperidin-3-yl)methyl)-N-(2-methoxyethyl)-2-oxo-2H-chromene-3-carboxamide

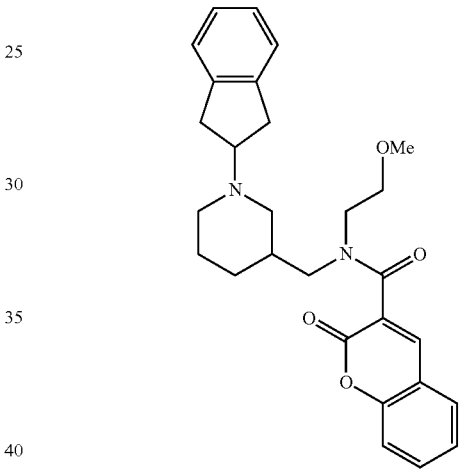

Step 1: Synthesis of (±)-N-((1-(2,3-dihydro-1H-inden-2-yl)piperidin-3-yl)methyl)-N-(2-methoxyethyl)-2-oxo-2H-chromene-3-carboxamide

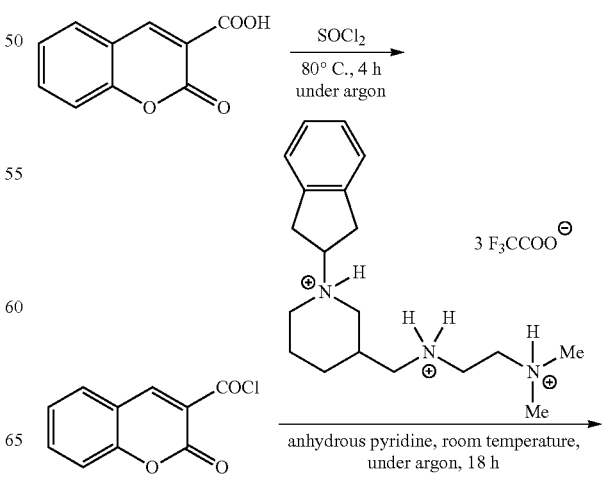

-continued

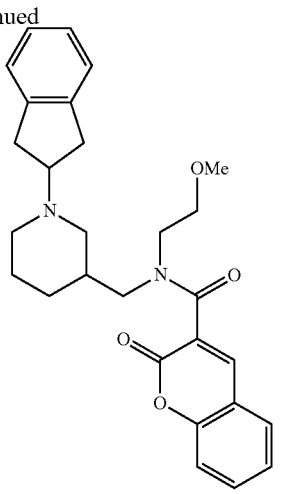

To a 50-mL round-bottomed flask with a stirring bar, 2-oxo-2H-chromene-3-carboxylic acid (0.323 g, 1.699 mmol) was added. Thionyl chloride (8 mL) was added at room temperature and the resulting solution was stirred under an atmosphere of argon at 80° C. for 4 h. The reaction mixture was evaporated and the residue was dried in vacuo. Anhydrous pyridine (10 mL) was added, followed by a solution of (±)-$N^1$-((1-(2,3-dihydro-1H-inden-2-yl)piperidin-3-yl)methyl)-$N^2$,$N^2$-dimethylethane-1,2-diamine tri(2,2,2-trifluoroacetate) (0.323 g, 0.502 mmol) in anhydrous pyridine (5 mL). After 18 h the reaction mixture was evaporated and the residue was dried in vacuo. $CH_2Cl_2$ (100 mL) was added the resulting solution was transferred into a 250-mL separating funnel and washed with sat. aq $NaHCO_3$ (2×70 mL), followed by sat. brine solution (150 mL), and dried over anhyd $Na_2SO_4$ and evaporated. The residue was purified by flash column chromatography using $CH_2Cl_2$-MeOH—$NH_3$ (25% aqueous solution) (9:1:0.003, v/v/v) to produce 0.044 g of (±)-N-((1-(2,3-dihydro-1H-inden-2-yl)piperidin-3-yl)methyl)-N-(2-methoxyethyl)-2-oxo-2H-chromene-3-carboxamide.

Product appearance: light orange oil

Yield: 19%

TLC: $R_f$=0.22 ($CH_2Cl_2$-MeOH—$NH_3$(25% aqueous solution)=9:1:0.003, v/v/v)

$^1$H-NMR (400 MHz, $CDCl_3$): δ=0.78-0.89 (0.5H, m), 1.09-1.20 (0.5H, m), 1.56-2.04 (5H, m), 2.06-2.14 (4H, m), 2.20-3.31 (1H, m), 2.34 (2H, s), 2.40-2.47 (1.5H, m), 2.62-2.66 (0.5H, m), 2.81-2.89 (1.5H, m), 2.97-3.45 (8.5H, m), 3.57-3.66 (1H, m), 7.11-7.21 (4H, m), 7.29-7.34 (1H, m), 7.36-7.38 (1H, m), 7.47-7.53 (1H, m), 7.56-7.61 (1H, m), 7.75-7.82 (1H, m).

$^{13}$C-NMR (100 MHz, $CDCl_3$): δ=24.62, 28.24, 28.44, 34.44, 35.34, 36.59, 36.80, 36.94, 43.59, 45.64, 45.71, 46.58, 47.81, 51.87, 52.03, 53.13, 55.68, 56.14, 57.60, 66.97, 67.35, 116.84, 118.20, 118.27, 124.29, 124.32, 124.38, 124.49, 125.81, 125.99, 126.38, 126.45, 128.32, 128.46, 132.57, 132.63, 141.34, 141.89, 142.10, 153.94, 157.94, 158.06, 165.32, 165.72.

HRMS (ESI+): m/z calculated for $C_{29}H_{36}N_3O_3$ 474.2757; found: 474.2750.

Example 3: Synthesis of (±)-N-((1-(2,3-dihydro-1H-inden-2-yl)piperidin-3-yl)methyl)-N-(2-(dimethylamino)ethyl)-8-hydroxyquinoline-7-carboxamide

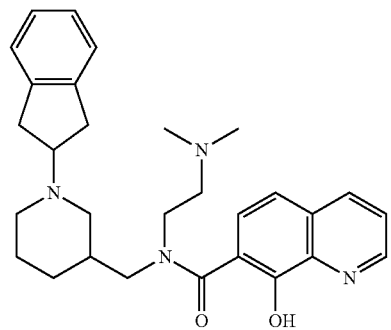 [SMILES: CN(C)CCN(CC1CCCN(C2Cc3ccccc3C2)C1)C(=O)c1ccc2cccnc2c1O]

Step 1: Synthesis of (±)-N-((1-(2,3-dihydro-1H-inden-2-yl)piperidin-3-yl)methyl)-N-(2-(dimethylamino)ethyl)-8-hydroxyquinoline-7-carboxamide

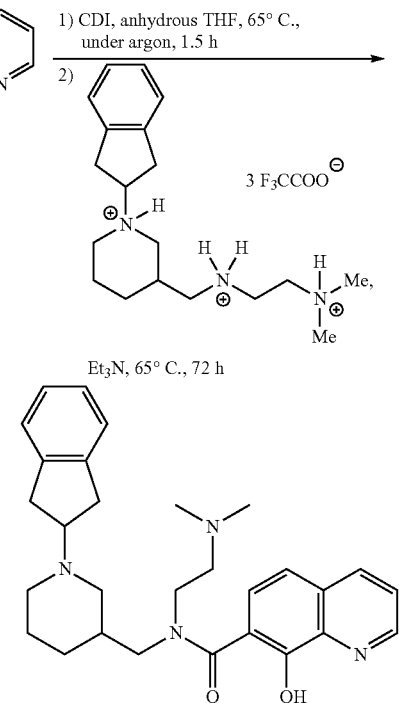

To a 50-mL round-bottomed flask with a stirring bar, 8-hydroxyquinoline-7-carboxylic acid (0.230 g, 1.216 mmol) and 1,1'-carbonyldiimidazole (CDI) (0.198 g, 1.221 mmol) was added. Anhydrous THF (15 mL) was added at room temperature and the resulting solution was stirred under an atmosphere of argon at 65° C. for 1.5 h. A solution of (±)-$N^1$-((1-(2,3-dihydro-1H-inden-2-yl)piperidin-3-yl)methyl)-$N^2$,$N^2$-dimethylethane-1,2-diamine tri(2,2,2-trifluoroacetate) (0.589 g, 0.915 mmola) and $Et_3N$ (0.675 mL, 4.870 mmol) in anhydrous THF (5 mL) was added and the reaction mixture was stirred at 65° C. for 72 h. The reaction mixture was evaporated and $CH_2Cl_2$ (50 mL) was added to residue. The resulting solution transferred into a 100-mL separating funnel and washed with sat. aq NaHCO₃ (3×50 mL), H₂O (2×50 mL), followed by sat. brine solution (50 mL), and dried over anhyd Na₂SO₄ and evaporated. The residue was purified by flash column chromatography using CH₂Cl₂-MeOH—NH₃(25% aqueous solution) (20:1:0.003, v/v/v; then 15:1:0.003, v/v/v) then crystallized from aceton to produce 0.024 g of (±)-N-((1-(2,3-dihydro-1H-inden-2-yl)piperidin-3-yl)methyl)-N-(2-(dimethylamino)ethyl)-8-hydroxyquinoline-7-carboxamide.

Product appearance: white solid
Yield: 6%
TLC: $R_f$=0.15 (CH₂Cl₂-MeOH—NH₃(25% aqueous solution)=9:1:0.003, v/v/v)

¹H-NMR (400 MHz, DMSO-d6): δ=0.53-0.61 (0.4H, m), 1.00-1.08 (0.6H, m), 1.23-1.53 (2.5H, m), 1.67-1.89 (6H, m), 2.00-2.08 (1.5H, m), 2.20-3.27 (3.5H, m), 2.62-2.67 (1.5H, m), 2.76-3.13 (7H, m), 3.22-3.27 (2H, m), 3.54-3.58 (1H, m), 7.09-7.23 (4.5 H, m), 7.31-7.33 (0.5H, m), 7.41-7.47 (1H, m), 7.60-7.63 (1H, m), 8.34-8.38 (1H, m), 8.88-8.91 (1H, m).

¹³C-NMR (100 MHz, DMSO-d6): δ=34.28, 34.69, 36.06, 36.38, 36.54, 44.93, 45.39, 45.79, 47.60, 51.34, 51.68, 52.06, 55.04, 55.43, 56.15, 57.38, 66.23, 66.82, 117.67, 117.77, 120.30, 120.71, 122.35, 124.07, 124.17, 124.30, 126.10, 126.35, 126.51, 128.43, 128.51, 136.17, 138.14, 141.46, 141.54, 141.66, 148.39, 148.63, 148.72, 168.36, 168.50.

HRMS (ESI+): m/z calculated for $C_{29}H_{37}N_4O_2$ 473.2917; found: 473.2927.

Synthesis of Compounds with General Formula (II)

Example 1: Synthesis of (±)-N-((1-(2,3-dihydro-1H-inden-2-yl)piperidin-3-yl)methyl)-N-(2-methoxyethyl)naphthalene-2-sulfonamide

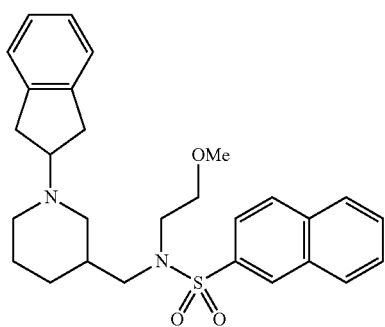 [SMILES: COCCN(CC1CCCN(C2Cc3ccccc3C2)C1)S(=O)(=O)c1ccc2ccccc2c1]

Step 1: Synthesis of (±)-1-benzoylpiperidine-3-carboxylic acid

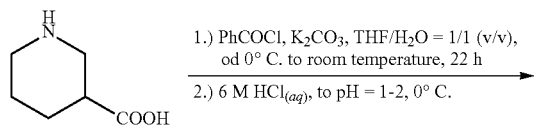

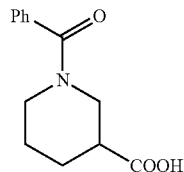

To a 250-mL round-bottomed flask equipped with a stirring bar, nipecotic acid (9.946 g, 77.007 mmol) was added. THF (80 mL), H₂O (80 mL) and K₂CO₃ (53.214 g, 385.023 mmol) were added, and the mixture was cooled to 0° C. A solution of benzoyl chloride (8.931 mL, 77.007 mmol, 1.0 equiv) in THF (35 mL) was added drop-wise. The reaction mixture was allowed to warm to r.t. and then stirred for 22 h. The reaction mixture was transferred into a 500-mL separating funnel and washed with EtOAc (3×150 mL). The aqueous phase was cooled to 0° C. and adjusted to pH 1-2 with 6 M aq HCl. The white precipitate was collected in a Büchner funnel under suction filtration, and then dried in vacuo at room temperature in the presence of NaOH, P₂O₅ and silica gel to constant mass to produce 17.028 g of (±)-1-benzoylpiperidine-3-carboxylic acid. This product was used in the next step without further purification.

Product appearance: white solid
Yield: 95%
Melting point: 171-175° C.
TLC: 0.53 (MeCN-MeOH—H₂O=3/1/1, v/v/v)
IR (ATR): 2865, 2563, 1709, 1584, 1564, 1464, 1277, 1212, 929, 861, 791, 729, 632, 572 cm⁻¹.

¹H NMR (400 MHz, DMSO-d6): δ=1.45-1.69 (3H, m), 1.96-2.00 (1H, m), 2.42-2.46 (1H, m), 3.00-3.17 (2H, m), 3.45-3.63 (1H, m), 4.13-4.43 (1H, m), 7.37-7.52 (5H, m), 12.44 (1H, bs).

¹³C NMR (100 MHz, DMSO-d6): δ=23.63, 24.40, 26.79, 40.63, 41.54, 43.41, 47.29, 48.72, 48.72, 126.64, 128.33, 129.32, 136.24, 169.14, 174.24.

HRMS (ESI⁺): m/z calculated for $C_{13}H_{16}NO_3$: 234.1130; found: 231.1129.

CHN analysis: calculated for $C_{13}H_{15}NO_3$: C, 66.94; H, 6.48; N, 6.00. Found: C, 67.15; H, 6.74; 6.16.

Step 2: Synthesis of (±)-1-benzoyl-N-(2-methoxyethyl)piperidine-3-carboxamide

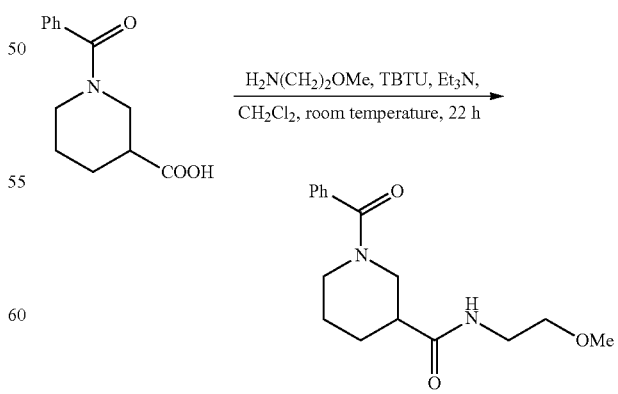

To a 250-mL round-bottomed flask equipped with a stirring bar, (±)-1-benzoylpiperidine-3-carboxylic acid (2.883 g, 12.359 mmol) and CH₂Cl₂ (160 mL) were added.

Et₃N (3.446 mL, 24.719 mmol, 2.0 equiv) was added drop-wise, followed by TBTU (3.969 g, 12.359 mmol). After 30 min, 2-methoxyethylamine (2.125 mL, 24.719 mmol) was added drop-wise, and the reaction mixture was stirred for 22 h. The reaction mixture was transferred into a 500-mL separating funnel and washed with H₂O (2×200 mL), 0.5 M aq HCl (2×200 mL), sat. aq NaHCO₃ solution (2×200 mL) followed by sat. brine solution (200 mL), and dried over anhyd Na₂SO₄ and evaporated, to produce 3.756 g of crude (±)-1-benzoyl-N-(2-methoxyethyl)piperidine-3-carboxamide. This product was used in the next step without further purification.

Product appearance: colorless oil

HRMS (ESI⁺): m/z calculated for $C_{16}H_{23}N_2O_3$: 291.1709; found: 291.1707.

Step 3: Synthesis of (±)-N-((1-benzylpiperidin-3-yl)methyl)-2-methoxyethan-1-amine

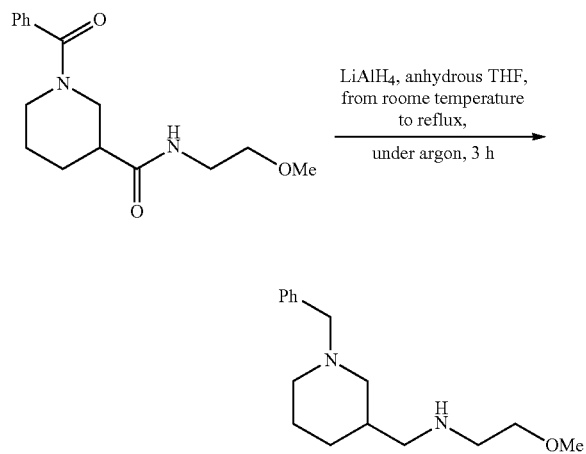

To a 250-mL tree-neck round-bottomed flask equipped with a stirring bar and a reflux condenser, LiAlH₄ (2.455 g, 64.679 mmol) was added under an argon atmosphere. Anhydrous THF (ca. 120 mL) was added with a double-tipped needle. A solution of crude (±)-1-benzoyl-N-(2-methoxyethyl)piperidine-3-carboxamide (3.756 g, 12.936 mmol) in anhydrous THF (ca. 40 mL) was added with a double-tipped needle, and the reaction mixture was refluxed for 3 h under an argon atmosphere. The mixture was then cooled to 0° C. and the excess hydride was decomposed by drop-wise addition of H₂O (2.455 mL) followed by 15% aq NaOH (2.455 mL) and then H₂O (7.365 mL). After vigorous stirring for 1 h at r.t., the mixture was filtered under suction and the white precipitate was washed thoroughly with THF (5×60 mL). The combined filtrates were evaporated to produce 2.794 g of crude (±)-N-((1-benzylpiperidin-3-yl)methyl)-2-methoxyethan-1-amine. This product was used in the next step without further purification.

Product appearance: slightly golden liquid

HRMS (ESI⁺): m/z calculated for $C_{16}H_{27}N_2O$: 263.2123; found: 263.2128.

Step 4: Synthesis of (±)-tert-butyl ((1-benzylpiperidin-3-yl)methyl)(2-methoxyethyl)carbamate

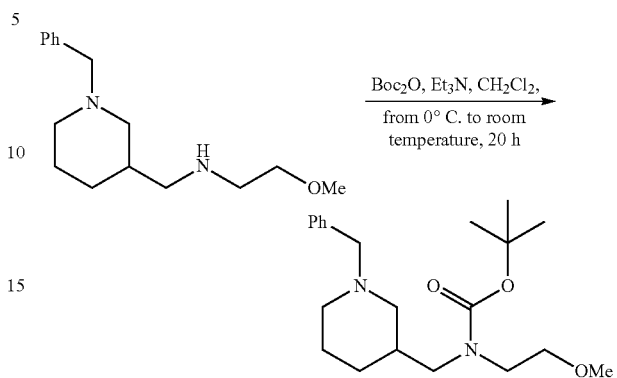

CH₂Cl₂ (50 mL) and a stirring bar were added to crude (±)-N-((1-benzylpiperidin-3-yl)methyl)-2-methoxyethan-1-amine (2.794 g, 10.648 mmol) in a 100-mL round-bottomed flask equipped with a stirring bar. Et₃N (1.484 mL, 10.648 mmol) was added drop-wise, and the reaction mixture was cooled to 0° C. A solution of Boc₂O (2.324 g, 10.648 mmol) in CH₂Cl₂ (10 mL) was added drop-wise, and the reaction mixture was allowed to warm to r.t. and then stirred for 20 h. The reaction mixture was transferred into a 100-mL separating funnel and washed with H₂O (30 mL), dried over anhyd. Na₂SO₄, and evaporated. The residue was purified by flash column chromatography using CH₂Cl₂-MeOH (30:1) then CH₂Cl₂-MeOH (10:1) as the eluent to produce 3.484 g of (±)-tert-butyl ((1-benzylpiperidin-3-yl)methyl)(2-methoxyethyl)carbamate.

Product appearance: slightly golden oil

Yield: 78% (from (±)-1-benzoylpiperidine-3-carboxylic acid)

TLC: $R_f$=0.53 (CH₂Cl₂-MeOH=10:1, v/v)

IR (ATR): 2973, 2929, 1690, 1412, 1364, 1244, 1158, 1116, 867, 738, 698, 560 cm⁻¹

¹H NMR (400 MHz, CDCl₃): δ=0.88-1.01 (1H, m), 1.43 (9H, s), 1.51-1.58 (1H, m), 1.62-1.72 (3H, m), 1.88-1.96 (2H, m), 2.74-2.79 (2H, m), 3.11-3.15 (2H, m), 3.24-3.36 (5H, m), 3.39-3.49 (4H, m), 7.21-7.38 (5H, m).

¹³C NMR (100 MHz, CDCl₃): δ=24.85, 28.32, 28.51, 35.54, 36.02, 47.03, 51.31, 51.89, 53.94, 54.15, 57.72, 58.05, 58.73, 63.54, 70.83, 71.03, 79.21, 79.32, 126.76, 126.80, 126.85, 128.03, 129.05, 129.10, 138.15, 138.35, 155.59.

HRMS (ESI⁺): m/z calculated for $C_{21}H_{35}N_2O_3$: 363.2648; found: 363.2638.

CHN analysis: calculated for $C_{21}H_{34}N_2O_3$: C, 69.58; H, 9.45; N, 7.73. Found: C, 69.75; H, 9.67; N, 7.86.

Step 5: Synthesis of (±)-tert-butyl (2-methoxyethyl)(piperidin-3-ylmethyl)carbamate

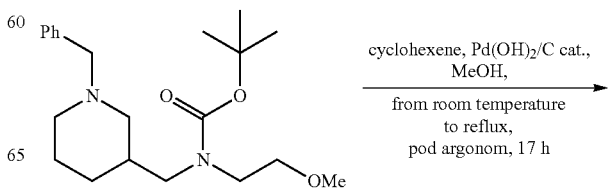

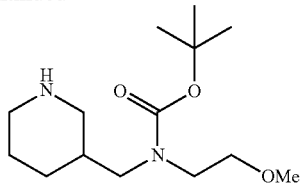

To a 250-mL round-bottomed flask with a stirring bar, (±)-tert-butyl ((1-benzylpiperidin-3-yl)methyl)(2-methoxyethyl)carbamate (4.137 g, 11.412 mmol) and MeOH (160 mL) were added at room temperature. The resulting solution was stirred and agitated with a stream of argon for 30 min. Pd(OH)$_2$ on carbon (20 wt. %) (0.828 g, 20% mass of (±)-tert-butyl ((1-benzylpiperidin-3-yl)methyl)(2-methoxyethyl)carbamate) was added, followed by cyclohexene (11.571 mL, 114.122 mmol). The resulting suspension was refluxed under an atmosphere of argon for 17 h, then filtered through a pad of Celite, and evaporated, to produce 3.015 g of crude amine (±)-tert-butyl (2-methoxyethyl)(piperidin-3-ylmethyl)carbamate. This product was used in the next step without further purification.

Product appearance: colorless oil
Yield: 97%
TLC: R$_f$=0.44 (CH$_2$Cl$_2$-MeOH-Et$_3$N=20:2:1, v/v/v)
$^1$H-NMR (400 MHz, CDCl$_3$): δ=1.00-1.14 (1H, m), 1.37-1.49 (10H, m), 1.60-1.80 (5H, m), 2.25-2.37 (1H, m), 2.51-2.58 (1H, m), 2.95-3.00 (2H, m), 3.13-3.25 (1H, m), 3.28-3.38 (5H, m), 3.44-3.52 (2H, m).
HRMS (ESI$^+$): m/z calculated for C$_{14}$H$_{29}$N$_2$O$_3$ 273.2178; found 273.2174.

Step 6: Synthesis of (±)-tert-butyl ((1-(2,3-dihydro-1H-inden-2-yl)piperidin-3-yl)methyl)(2-methoxyethyl)carbamate

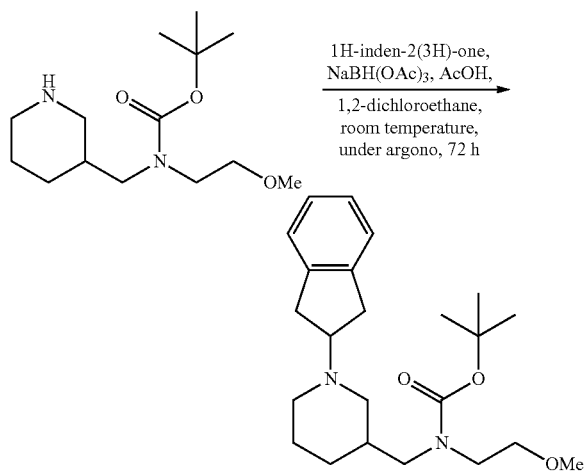

To a 100-mL round-bottomed flask with a stirring bar, (±)-tert-butyl (2-methoxyethyl)(piperidin-3-ylmethyl)carbamate (1.094 g, 4.016 mmol) and 1,2-dichloroethane (50 mL) were added at room temperature. The resulting solution was stirred and agitated with a stream of argon for 15 min. NaBH(OAc)$_3$ (1.596 g, 7.530 mmol), 1H-inden-2(3H)-one (0.531 g, 4.018 mmol) and AcOH (0.230 mL, 4.018 mmol) were added, and the resulting suspension was stirred under an atmosphere of argon for 72 h. The reaction mixture was opened to the air and quenched with saturated aqueous NaHCO$_3$ solution (50 mL). The mixture was transferred into a 250-mL separating funnel, and CH$_2$Cl$_2$ (20 mL) was added. The separating funnel was shaken vigorously and the organic phase was separated, dried over anhydrous Na$_2$SO$_4$, and evaporated. The residue was purified by flash column chromatography using CH$_2$Cl$_2$/MeOH (30:1, v/v) as the eluent, to produce 1.292 g of (±)-tert-butyl ((1-(2,3-dihydro-1H-inden-2-yl)piperidin-3-yl)methyl)(2-methoxyethyl)carbamate.

Product appearance: slightly golden oil
Yield: 83%
TLC: R$_f$=0.50 (CH$_2$Cl$_2$/MeOH, 10:1, v/v)
IR (ATR): 2930, 2359, 1692, 1463, 1414, 1365, 1170, 1117, 1010, 867, 743, 526 cm$^{-1}$
$^1$H-NMR (400 MHz, DMSO-d6, 60° C.): δ=0.90-0.99 (1H, m), 1.40 (9H, s), 1.56-1.67 (2H, m), 1.77-1.88 (2H, m), 2.01-2.07 (1H, m), 2.73-2.81 (4H, m), 2.95-3.02 (2H, m), 3.10 (2H, d, J=6.90 Hz), 3.14-3.15 (3H, m), 3.25 (3H, s), 3.28-3.31 (1H, m), 3.41-3.44 (2H, m), 7.07-7.12 (2H, m), 7.15-7.19 (2H, m).
$^{13}$C-NMR (100 MHz, DMSO-d6, 60° C.): δ=24.08, 27.70, 27.85, 35.92, 36.02, 46.29, 51.18, 54.95, 57.67, 66.13, 78.09, 123.76, 125.78, 141.04, 141.10, 154.52.
HRMS (ESI+): m/z calculated for C$_{23}$H$_{37}$N$_2$O$_3$ 389.2804; found 389.2798.

Step 7: Synthesis of (±)-N-((1-(2,3-dihydro-1H-inden-2-yl)piperidin-3-yl)methyl)-2-methoxyethan-1-amine di(2,2,2-trifluoroacetate)

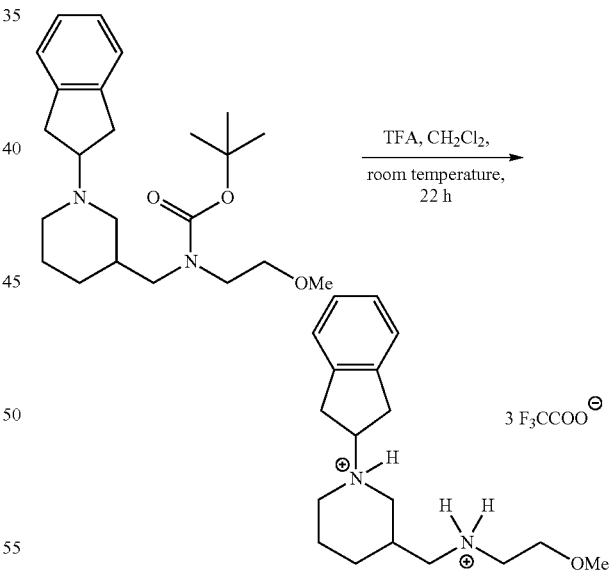

To a 100-mL round-bottomed flask equipped with a stirring bar, (f)-tert-butyl ((1-(2,3-dihydro-1H-inden-2-yl)piperidin-3-yl)methyl)(2-methoxyethyl)carbamate (1.203 g, 3.096 mmol) and CH$_2$Cl$_2$ (50 mL) were added at room temperature. The resulting solution was stirred and TFA (2.371 mL, 30.960 mmol) was added drop-wise. After 22 h, the reaction mixture was evaporated. The residue was co-evaporated with CH$_2$Cl$_2$ (2×40 mL), followed by n-hexane (2×50 mL). Et$_2$O (50 mL) was added to the oily residue, and the flask was placed in an ultrasonic bath for 15 min. During this time, the oily residue transformed into a white solid. The flask was removed from the ultrasonic bath and the precipitate was allowed to settle to the bottom of the flask. The supernatant was removed, Et$_2$O (30 mL) was added, and the flask was placed back in the ultrasonic bath for 1 min. The flask was removed from the ultrasonic bath and the precipitate was allowed to settle to the bottom of the flask. The supernatant was removed, Et$_2$O (30 mL) was added again, and this procedure was repeated two more times. After the final supernatant was removed, the solid residue was dried at reduced pressure. This product was used in the next step without further purification.

Product appearance: white solid
HRMS (ESI+): m/z calculated for C$_{18}$H$_{29}$N$_2$O 289.2280; found 289.2274.

Step 8: Synthesis of (±)-N-((1-(2,3-dihydro-1H-inden-2-yl)piperidin-3-yl)methyl)-N-(2-methoxyethyl)naphthalene-2-sulfonamide

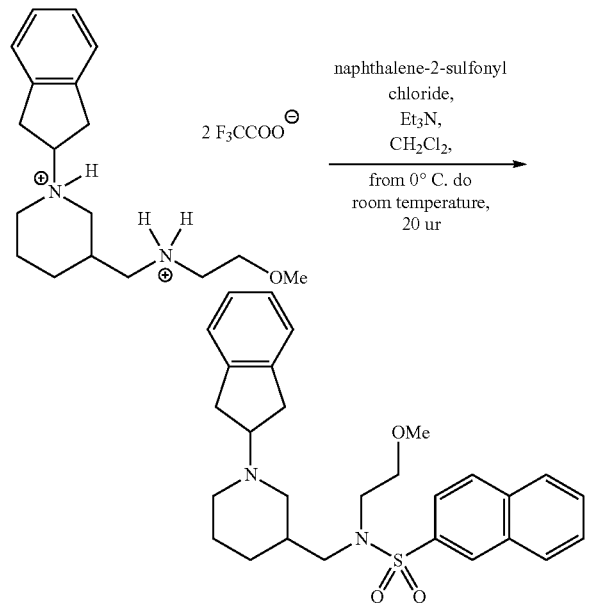

To a 25-mL round-bottomed flask equipped with a stirring bar, (±)-N-((1-(2,3-dihydro-1H-inden-2-yl)piperidin-3-yl)methyl)-2-methoxyethan-1-amine di(2,2,2-trifluoroacetate) (0.256 g, 0.496 mmol) and CH$_2$Cl$_2$ (10 mL) were added at room temperature. The resulting suspension was stirred and Et$_3$N (0.207 mL, 1.487 mmol) was added drop-wise, followed by naphthalene-2-sulfonyl chloride (0.113 g, 0.496 mmol) and the reaction mixture was allowed to warm to r.t. and then stirred for 20 h. The reaction mixture was transferred into a 50-mL separating funnel, CH$_2$Cl$_2$ (15 mL) was added and washed with H$_2$O (20 mL), followed by saturated aqueous NaHCO$_3$ solution (20 mL). The organic phase was dried over anhyd Na$_2$SO$_4$, and evaporated. The residue was purified by flash column chromatography using CH$_2$Cl$_2$-MeOH (20:1, v/v) as the eluent to produce 0.220 g (±)-N-((1-(2,3-dihydro-1H-inden-2-yl)piperidin-3-yl)methyl)-N-(2-methoxyethyl)naphthalene-2-sulfonamide.

Product appearance: slightly golden oil
Yield: 93%
TLC: R$_f$=0.51 (CH$_2$Cl$_2$/MeOH, 10:1, v/v)

IR (ATR): 2928, 1687, 1589, 1456, 1334, 1154, 1115, 1072, 991, 858, 816, 743, 649, 614 cm$^{-1}$ $^1$H-NMR (400 MHz, CDCl$_3$): δ=0.92-1.03 (1H, m), 1.58-1.77 (4H, m), 1.97-2.06 (2H, m), 2.82-3.06 (6H, m), 3.09-3.21 (3H, m), 3.24 (3H, s), 3.34-3.41 (2H, m), 3.49-3.55 (2H, m), 7.11-7.17 (4H, m), 7.59-7.66 (2H, m), 7.80 (1H, dd, J$_1$=8.7 Hz, J$_2$=1.9 Hz), 7.88-7.98 (3H, m), 8.40 (1H, d, J=1.4 Hz).

$^{13}$C-NMR (100 MHz, CDCl$_3$): δ=24.70, 28.41, 34.73, 36.72, 36.95, 47.81, 52.06, 53.20, 55.92, 58.58, 67.07, 70.96, 122.42, 124.16, 124.21, 126.16, 127.34, 127.69, 128.24, 128.50, 128.99, 129.08, 131.97, 134.49, 136.39, 141.38.

HRMS (ESI+): m/z calculated for C$_{28}$H$_{35}$N$_2$O$_3$S 479.2368; found 479.2354.

Example 2: Synthesis of (±)-N-((1-benzylpiperidin-3-yl)methyl)-N-(2-methoxyethyl)naphthalene-2-sulfonamide Step 1: Synthesis of (±)-N-((1-benzylpiperidin-3-yl)methyl)-N-(2-methoxyethyl)naphthalene-2-sulfonamide

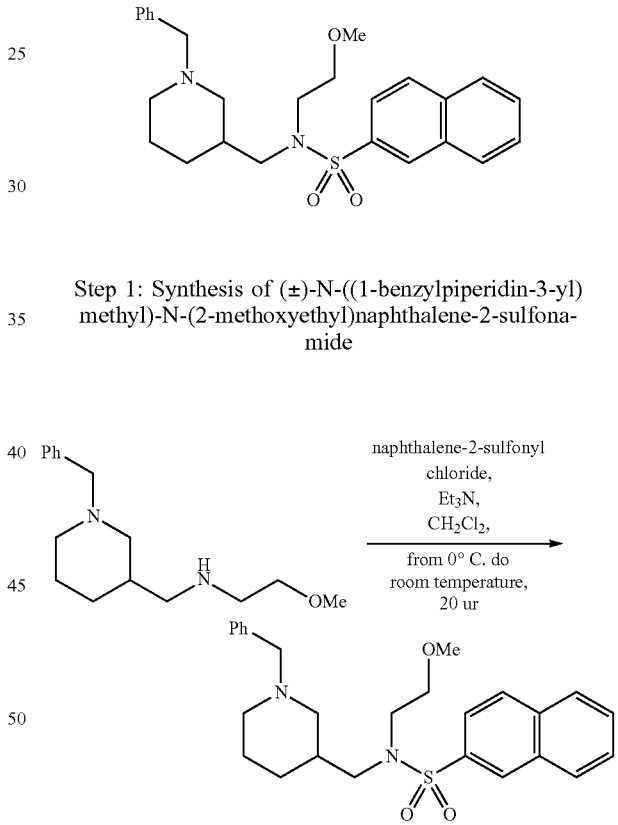

To a 50-mL round-bottomed flask equipped with a stirring bar, (±)-N-((1-benzylpiperidin-3-yl)methyl)-2-methoxyethan-1-amine (1.062 g, 4.047 mmol) and CH$_2$Cl$_2$ (25 mL) were added at room temperature. The resulting solution was stirred and cooled to 0° C. Et$_3$N (0.564 mL, 4.047 mmol) was added drop-wise, followed by naphthalene-2-sulfonyl chloride (0.918 g, 4.047 mmol) and the reaction mixture was allowed to warm to r.t. and then stirred for 20 h. The reaction mixture was transferred into a 100-mL separating funnel, CH$_2$Cl$_2$ (25 mL) was added and washed with H$_2$O (40 mL), followed by saturated aqueous NaHCO$_3$ solution (40 mL). The organic phase was dried over anhyd Na$_2$SO$_4$, and evaporated. The residue was purified by flash column chromatography using $CH_2Cl_2$-MeOH (30:1, v/v) as the eluent to produce 1.654 g (±)-N-((1-benzylpiperidin-3-yl)methyl)-N-(2-methoxyethyl)naphthalene-2-sulfonamide.

Product appearance: colorless oil
Yield: 90%
TLC: $R_f$=0.57 ($CH_2Cl_2$/MeOH, 10:1, v/v)
IR (ATR): 2928, 2803, 1452, 1333, 1154, 1115, 1072, 983, 883, 859, 817, 732, 699, 650, 615 cm$^{-1}$
$^1$H-NMR (400 MHz, CDCl$_3$): δ=0.95-1.04 (1H, m), 1.54 (1H, bs), 1.66-1.74 (3H, m), 1.98 (2H, bs), 2.76 (2H, d, J=30.4 Hz), 3.06-3.16 (2H, m), 3.21 (3H, s), 3.30 (2H, t, J=6.3 Hz), 3.45-3.48 (4H, m), 7.23-7.30 (5H, m), 7.59-7.66 (2H, m), 7.76 (1H, dd, =8.6 Hz, J$_2$=1.8 Hz), 7.89-7.97 (3H, m), 8.38 (1H, d, J=1.4 Hz).
$^{13}$C-NMR (100 MHz, CDCl$_3$): δ=24.54, 28.21, 34.82, 48.04, 53.21, 53.89, 57.60, 58.66, 63.44, 71.10, 122.52, 126.85, 127.39, 127.78, 128.05, 128.36, 128.56, 129.07, 129.11, 129.14, 132.07, 134.59, 136.40, 138.25.
HRMS (ESI+): m/z calculated for $C_{26}H_{33}N_2O_3S$ 453.2212; found 453.2209.

Example 3: Synthesis of N-((1-benzylpiperidin-3-yl)methyl)naphthalene-2-sulfonamide

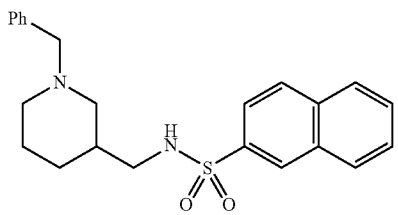 [SMILES: O=S(=O)(NCC1CCCN(Cc2ccccc2)C1)c1ccc2ccccc2c1]

Step 1: Synthesis of (±)-1-benzoylpiperidine-3-carboxamide

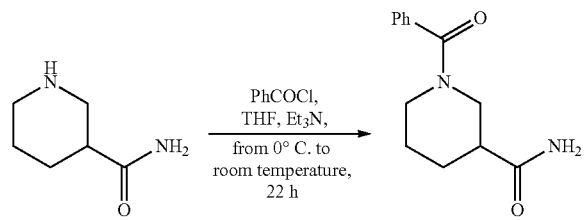 [SMILES: NC(=O)C1CCCNC1 ; NC(=O)C1CCCN(C(=O)c2ccccc2)C1]

To a 500-mL round-bottomed flask equipped with a stirring bar, nipecotamide (10.000 g, 78.020 mmol) and THF (260 mL) were added. The suspension was cooled to 0° C. and Et$_3$N (10.875 mL, 78.020 mmol) was added drop-wise. A solution of benzoyl chloride (9.049 mL, 78.020 mmol) in THF (30 mL) was added drop-wise. The reaction mixture was allowed to warm to r.t. and then stirred for 22 h. The solvent was evaporated, the residue dissolved in H$_2$O (200 mL) and transferred into a 500 mL separating funnel, and washed with CH$_2$Cl$_2$ (3×300 mL). The combined organic phases were dried over anhyd Na$_2$SO$_4$, and evaporated, to produce 17.809 g of (±)-1-benzoylpiperidine-3-carboxamide. This product was used in the next step without further purification.

Product appearance: slightly yellow solid
Yield: 98%
Melting point: 171-173° C.
TLC: $R_f$=0.58 ($CH_2Cl_2$-MeOH=5:1, v/v)
IR (ATR): 3339, 3139, 2938, 2360, 1670, 1617, 1442, 1271, 1102, 936, 855, 670, 577 cm$^{-1}$
$^1$H NMR (400 MHz, DMSO-d6): δ=1.38 (1H, bs), 1.53-1.75 (2H, m), 1.91 (1H, bs), 2.30 (1H, bs), 2.78-3.08 (2H, m), 3.49-3.56 (1H, m), 4.35-4.46 (1H, m), 6.85-6.90 (1H, m), 7.29-7.52 (6H, m).
$^{13}$C NMR (100 MHz, DMSO-d6): δ=23.98, 24.80, 27.54, 27.79, 41.59, 41.60, 42.23, 43.99, 47.33, 49.35, 126.61, 128.36, 129.32, 136.20, 169.01, 174.52, 174.64.
HRMS (ESI$^+$): m/z calculated for $C_{13}H_{17}N_2O_2$: 233.1290; found: 233.1296.
CHN analysis: Calculated for $C_{13}H_{16}N_2O_2$: C, 67.22; H, 6.94; N, 12.06. Found: C, 67.58; H, 7.01; N, 12.11.

Step 2: Synthesis of (±)-(1-benzylpiperidin-3-yl)methanamine

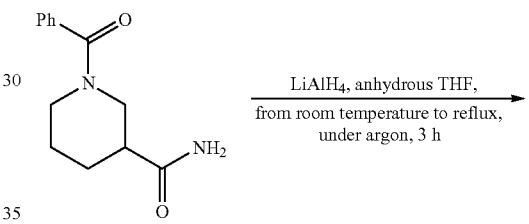

To a 250-mL tree-neck round-bottomed flask equipped with a stirring bar and a reflux condenser, LiAlH$_4$ (2.879 g, 75.863 mmol) was added under an argon atmosphere. Anhydrous THF (ca. 150 mL) was added with a double-tipped needle. Then (±)-1-benzoylpiperidine-3-carboxamide (3.524 g, 15.171 mmol) was added in small portions over 1 h, and the reaction mixture was refluxed for 3 h under an argon atmosphere. The mixture was then cooled to 0° C. and the excess hydride was decomposed by drop-wise addition of H$_2$O (2.879 mL) followed by 15% aq NaOH (2.879 mL) and then H$_2$O (8.637 mL). After vigorous stirring for 1 h at r.t., the mixture was filtered under suction and the white precipitate was washed thoroughly with THF (5×60 mL). The combined filtrates were evaporated, to produce 3.085 g of crude (±)-(1-benzylpiperidin-3-yl)methanamine. This product was used in the next step without further purification.

Product appearance: slightly golden liquid
HRMS (ESI$^+$): m/z calculated for $C_{13}H_{21}N_2$: 205.1705; found: 205.1710.

Step 3: Synthesis of (±)-N-((1-benzylpiperidin-3-yl)methyl)naphthalene-2-sulfonamide

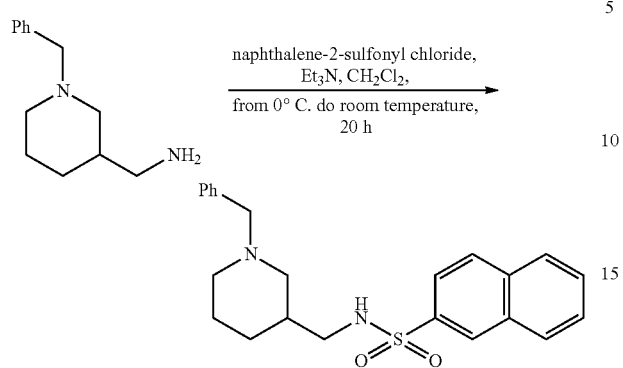

To a 50-mL round-bottomed flask equipped with a stirring bar, (±)-(1-benzylpiperidin-3-yl)methanamine (1.553 g, 7.503 mmol) and CH$_2$Cl$_2$ (50 mL) were added at room temperature. The resulting solution was stirred and cooled to 0° C. Et$_3$N (1.046 mL, 7.503 mmol) was added drop-wise, followed by naphthalene-2-sulfonyl chloride (1.723 g, 7.503 mmol) and the reaction mixture was allowed to warm to r.t. and then stirred for 20 h. The reaction mixture was transferred into a 100-mL separating funnel and washed with H$_2$O (40 mL), followed by saturated aqueous NaHCO$_3$ solution (40 mL). The organic phase was dried over anhyd Na$_2$SO$_4$, and evaporated. The residue was purified by flash column chromatography using CH$_2$Cl$_2$-MeOH (20:1, v/v) as the eluent to produce 1.288 g of (±)-N-((1-benzylpiperidin-3-yl)methyl)naphthalene-2-sulfonamide.

Product appearance: white solid
Yield: 43%
TLC: R$_f$=0.43 (CH$_2$Cl$_2$-MeOH=10:1, v/v)
IR (ATR): 3062, 2938, 2816, 2769, 1467, 1452, 1328, 1159, 1068, 972, 817, 759, 701, 658, 640, 614 cm$^{-1}$
$^1$H-NMR (400 MHz, CDCl$_3$): δ=1.02-1.11 (1H, m), 1.45-1.55 (1H, m), 1.60-1.71 (2H, m), 1.76-1.90 (2H, m), 2.09-2.15 (1H, m), 2.52-2.67 (2H, m), 2.85-2.97 (2H, m), 3.38-3.46 (2H, m), 5.20 (1H, bs), 7.22-7.31 (5H, m), 7.59-7.67 (2H, m), 7.78 (1H, dd, J$_1$=8.7 Hz, J$_2$=1.9 Hz), 7.90-7.97 (3H, m), 8.41 (1H, t, J=0.9 Hz)
$^{13}$C-NMR (100 MHz, CDCl$_3$): δ=24.07, 28.06, 35.36, 47.02, 53.78, 57.14, 63.23, 122.23, 126.95, 127.41, 127.80, 128.11, 128.26, 128.60, 129.05, 129.12, 129.38, 132.03, 134.62, 136.64, 137.77.
HRMS (ESI+): m/z calculated for C$_{23}$H$_{27}$N$_2$O$_2$S: 395.1793; found: 395.1784.

Example 4: Synthesis of N-((1-benzylpiperidin-3-yl)methyl)-N-methylnaphthalene-2-sulfonamide

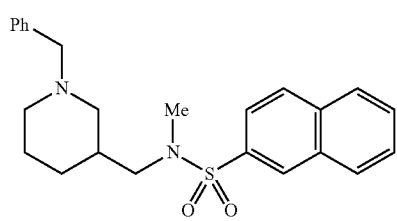 [SMILES: CN(CC1CCCN(Cc2ccccc2)C1)S(=O)(=O)c1ccc2ccccc2c1]

Step 1: Synthesis of (±)-N-((1-benzylpiperidin-3-yl)methyl)-N-methylnaphthalene-2-sulfonamide

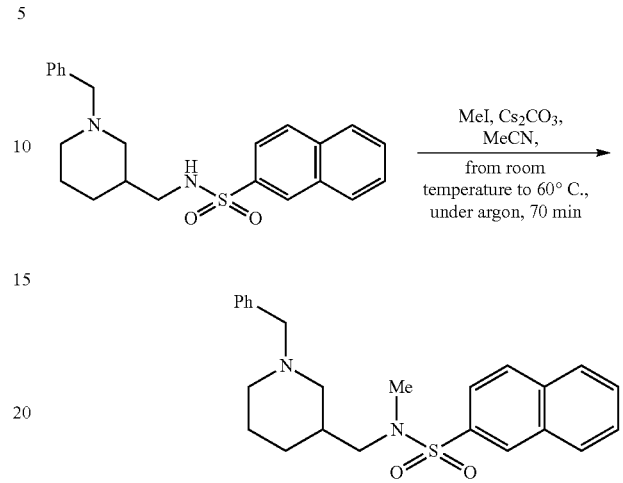

To a 25-mL round-bottomed flask equipped with a stirring bar, (±)-N-((1-benzylpiperidin-3-yl)methyl)naphthalene-2-sulfonamide (0.104 g, 0.264 mmol) and MeCN (10 mL) were added at room temperature. The resulting solution was stirred and agitated with a stream of argon for 15 min. Cs$_2$CO$_3$ (0,258 g, 0,792 mmol), MeI (0.050 mL, 0,792 mmol) and NaI (catalytic amount) were added and the resulting suspension was stirred for 70 min at 60° C. under an argon atmosphere. The reaction mixture was evaporated, and CH$_2$Cl$_2$ (20 mL) was added to the residue. The mixture was transferred to a 50-mL separating funnel and washed with H$_2$O (20 mL), followed by saturated aqueous NaHCO$_3$ solution (20 mL). The organic phase was dried over anhyd Na$_2$SO$_4$, and evaporated. The residue was purified by flash column chromatography using CH$_2$Cl$_2$-MeOH (24:1, v/v) as the eluent to produce 0.076 g of (±)-N-((1-benzylpiperidin-3-yl)methyl)-N-methylnaphthalene-2-sulfonamide.

Product appearance: white solid

Yield: 70%

TLC: R$_f$=0.29 (CH$_2$Cl$_2$-MeOH=20:1, v/v)

IR (ATR): 2937, 2809, 1453, 1334, 1155, 1132, 1070, 960, 889, 740, 653 cm$^{-1}$ $^1$H-NMR (400 MHz, CDCl$_3$): δ=1.00-1.10 (1H, m), 1.66-1.77 (3H, m), 1.82-2.04 (3H, m), 2.74 (4H, s), 2.84-2.97 (3H, m), 3.43-3.60 (2H, m), 7.21-7.25 (1H, m), 7.30 (4H, d, J=4.4 Hz), 7.60-7.67 (2H, m), 7.74 (1H, dd, J$_1$=8.6, J$_2$=1.8 Hz), 7.90-7.99 (3H, m), 8.34-8.35 (1H, s).

$^{13}$C-NMR (100 MHz, CDCl$_3$): δ=24.48, 28.12, 34.20, 35.23, 53.78, 57.68, 63.38, 122.63, 126.88, 127.43, 127.81, 128.08, 128.53, 128.60, 120.09, 129.17, 132.11, 134.33, 134.63, 138.13.

HRMS (ESI+): m/z calculated for C$_{24}$H$_{29}$N$_2$O$_2$S: 409.1950; found: 409.1939.

Example 5: Synthesis of (±)-N-((1-(3-fluorobenzyl)piperidin-3-yl)methyl)-N-(2-methoxyethyl)naphthalene-2-sulfonamide

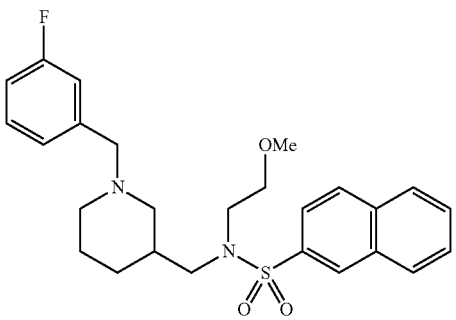 [SMILES: COCCN(CC1CCCN(Cc2cccc(F)c2)C1)S(=O)(=O)c1ccc2ccccc2c1]

Step 1: Synthesis of (±)-tert-butyl ((1-(3-fluorobenzyl)piperidin-3-yl)methyl)(2-methoxyethyl)carbamate

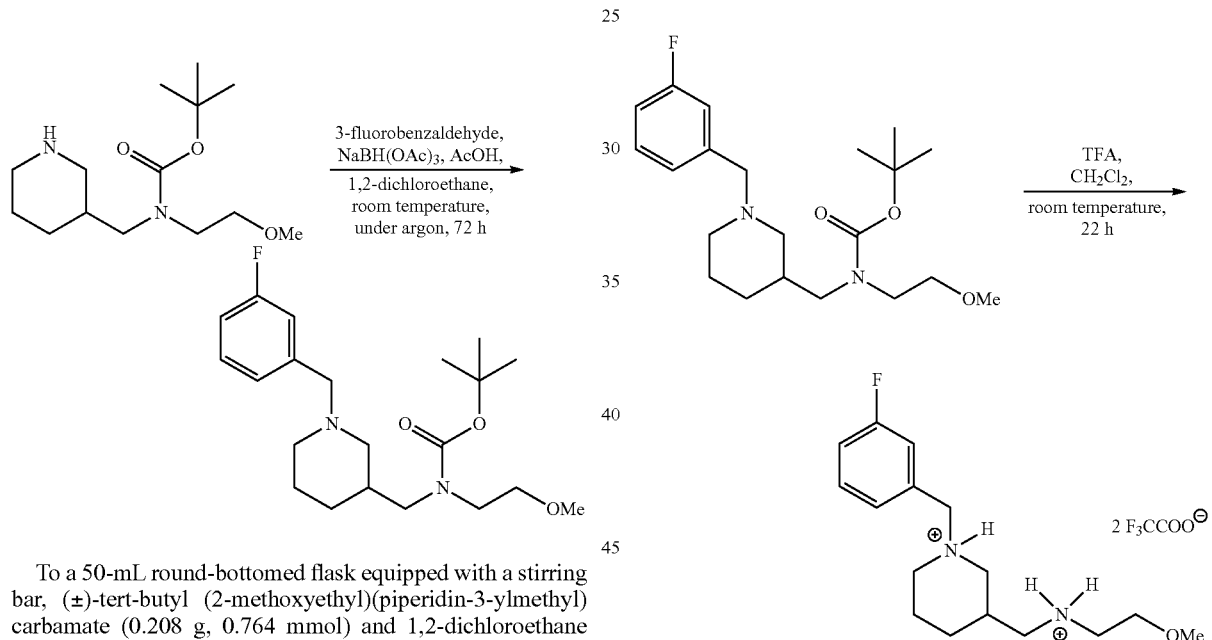

To a 50-mL round-bottomed flask equipped with a stirring bar, (±)-tert-butyl (2-methoxyethyl)(piperidin-3-ylmethyl)carbamate (0.208 g, 0.764 mmol) and 1,2-dichloroethane (15 mL) were added at room temperature. The resulting solution was stirred and agitated with a stream of argon for 15 min. NaBH(OAc)₃ (0,283 g, 1,335 mmol), 3-fluorobenzaldehid (0.083 mL, 0.764 mmol) and AcOH (0.044 mL, 0,764 mmol) were added, and the resulting suspension was stirred under an atmosphere of argon for 72 h. The reaction mixture was opened to the air and quenched with saturated aqueous NaHCO₃ solution (30 mL). The mixture was transferred into a 100-mL separating funnel, and CH₂Cl₂ (20 mL) was added. The separating funnel was shaken vigorously and the organic phase was separated, dried over anhydrous Na₂SO₄, and evaporated. The residue was purified by flash column chromatography using CH₂Cl₂/MeOH (28:1, v/v) as the eluent, to produce 0.184 g of (±)-tert-butyl ((1-(3-fluorobenzyl)piperidin-3-yl)methyl)(2-methoxyethyl)carbamate.

Product appearance: slightly golden oil
Yield: 63%
TLC: $R_f$=0.46 (CH₂Cl₂-MeOH=10:1, v/v)

IR (ATR): 2974, 2931, 1689, 1590, 1484, 1451, 1412, 1391, 1365, 1250, 1161, 1117, 777 cm$^{-1}$ $^{1}$H-NMR (400 MHz, CDCl₃): δ=0.89-1.00 (1H, m), 1.42-1.46 (10H, m), 1.63-1.77 (3H, m), 1.87-1.98 (2H, m), 2.72-2.75 (2H, m), 3.11-3.16 (2H, m), 3.24-3.37 (5H, m), 3.39-3.49 (4H, m), 6.89-6.94 (1H, m), 7.03-7.06 (2H, m), 7.21-7.25 (1H, m).

$^{13}$C-NMR (100 MHz, CDCl₃): δ=24.88, 28.37, 28.49, 35.63, 36.11, 47.16, 51.37, 51.93, 54.07, 54.23, 57.76, 58.12, 58.81, 62.96, 70.95, 71.13, 79.33, 79.43, 113.77 (d, $^{2}J$=21.3 Hz), 115.64 (d, $^{2}J$=21.3 Hz), 124.47 (d, $^{4}J$=2.9 Hz), 129.49 (d, $^{3}J$=8.1 Hz), 141.26 (d, $^{3}J$=8.1 Hz), 155.66, 162.86 (d, $^{1}J$=245.76 Hz).

HRMS (ESI+): m/z calculated for C₂₁H₃₄N₂O₃F: 381.2553; found: 381.2558.

Step 2: Synthesis of (±)-N-((1-(3-fluorobenzyl)piperidin-3-yl)methyl)-2-methoxyethanamine di(2,2,2-trifluoroacetate)

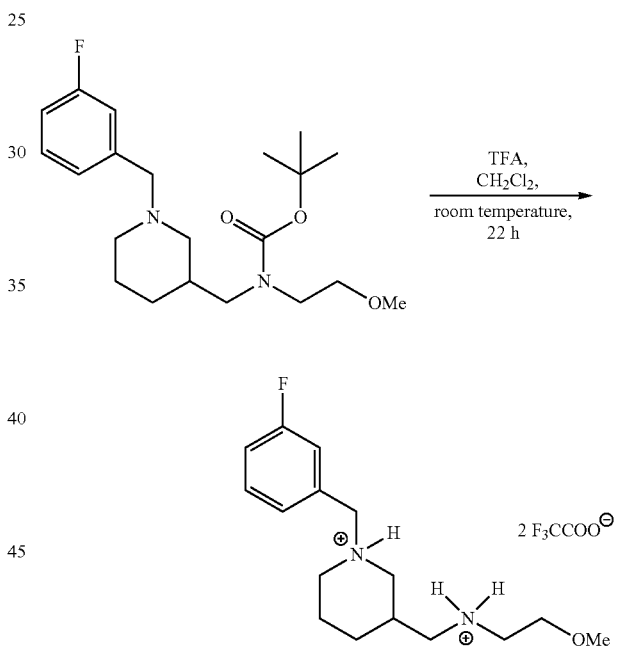

To a 25-mL round-bottomed flask with a stirring bar, (±)-tert-butyl ((1-(3-fluorobenzyl)piperidin-3-yl)methyl)(2-methoxyethyl)carbamate (0.133 g, 0.350 mmol) and CH₂Cl₂ (10 mL) were added at room temperature. The solution was stirred and TFA (0.270 mL, 3,500 mmol) was added dropwise. After 22 h the reaction mixture was evaporated and the residue was coevaporated with CH₂Cl₂ (2×15 mL), followed by n-hexane (2×15 mL) to produce 0.163 g of (±)-N-((1-(3-fluorobenzyl)piperidin-3-yl)methyl)-2-methoxyethanamine di(2,2,2-trifluoroacetate). This product was used in the next step without further purification.

Product appearance: slightly golden oil
Yield: 92%
HRMS (ESI+): m/z calculated for C₁₆H₂₅N₂OF 281.2029; found 281.2034.

Step 3: Synthesis of (±)-N-((1-(3-fluorobenzyl)piperidin-3-yl)methyl)-N-(2-methoxyethyl)naphthalene-2-sulfonamide

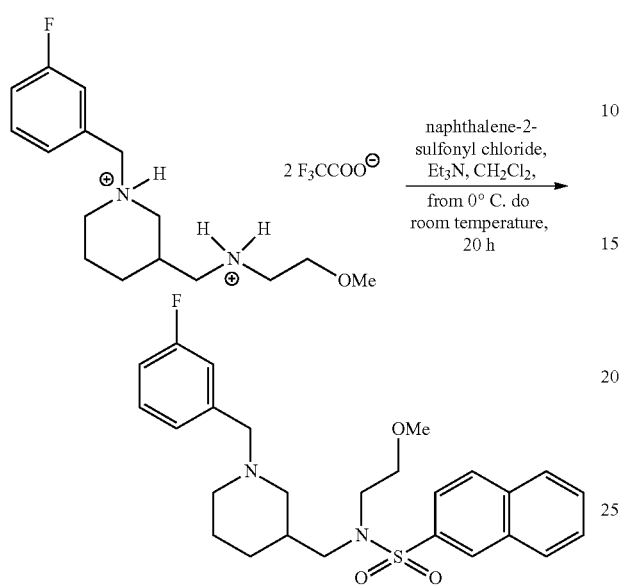

To a 50-mL round-bottomed flask equipped with a stirring bar, (±)-N-((1-(3-fluorobenzyl)piperidin-3-yl)methyl)-2-methoxyethanamine di(2,2,2-trifluoroacetate) (0.150 g, 0.295 mmol) and CH$_2$Cl$_2$ (20 mL) were added at room temperature. The resulting solution was stirred and cooled to 0° C. Et$_3$N (0.123 mL, 0.885 mmol) was added drop-wise, followed by naphthalene-2-sulfonyl chloride (0.067 g, 0.295 mmol) and the reaction mixture was allowed to warm to r.t. and then stirred for 20 h. The reaction mixture was transferred into a 50-mL separating funnel and washed with H$_2$O (20 mL), followed by saturated aqueous NaHCO$_3$ solution (20 mL). The organic phase was dried over anhyd Na$_2$SO$_4$, and evaporated. The residue was purified by flash column chromatography using CH$_2$Cl$_2$-MeOH (28:1, v/v) as the eluent to produce 0.121 g of (±)-N-((1-(3-fluorobenzyl)piperidin-3-yl)methyl)-N-(2-methoxyethyl)naphthalene-2-sulfonamide.

Product appearance: slightly golden oil
Yield: 87%
TLC: R$_f$=0.46 (CH$_2$Cl$_2$-MeOH=15:1, v/v)
IR (ATR): 2932, 1589, 1449, 1335, 1252, 1155, 1129, 1116, 1072, 748, 728, 651, 615 cm$^{-1}$ $^1$H-NMR (400 MHz, CDCl$_3$): δ=0.96-1.06 (1H, m), 1.49-1.55 (1H, m), 1.66-1.78 (3H, m), 1.95-2.01 (2H, m), 2.66-2.79 (2H, m), 3.11-3.13 (2H, m), 3.22 (3H, s), 3.28-3.33 (2H, m), 3.42-3.51 (4H, m), 6.90-6.95 (1H, m), 7.02-7.06 (2H, m), 7.21-7.25 (1H, m), 7.59-7.66 (2H, m), 7.76 (1H, dd, J$_1$=8.7 Hz, J$_2$=1.9 Hz), 7.89-7.97 (3H, m), 8.37-8.38 (1H, m).
$^{13}$C-NMR (100 MHz, CDCl$_3$): δ=24.54, 28.17, 34.85, 48.18, 53.25, 53.99, 57.65, 58.71, 62.73, 71.23, 113.74 (d, $^2$J=21.3 Hz), 115.57 (d, $^2$J=21.3 Hz), 122.54, 124.44 (d, $^4$J=2.9 Hz), 127.45, 127.83, 128.42, 128.62, 129.16, 129.21, 129.50 (d, $^3$J=8.1 Hz), 132.12, 134.65, 136.39, 141.36 (d, $^3$J=8.1 Hz), 162.86 (d, $^1$J=245.0 Hz).
HRMS (ESI+): m/z calculated for C$_{26}$H$_{32}$N$_2$O$_3$SF: 471.2118; found: 471.2110.

Example 6: Synthesis of N-((1-(2,3-dihydro-1H-inden-2-yl)piperidin-4-yl)methyl)-N-(2-methoxyethyl)naphthalene-2-sulfonamide

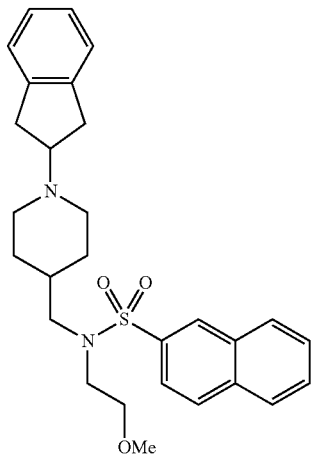 [SMILES: COCCN(CC1CCN(C2Cc3ccccc3C2)CC1)S(=O)(=O)c1ccc2ccccc2c1]

Step 1: Synthesis of 1-benzoylpiperidine-4-carboxylic acid

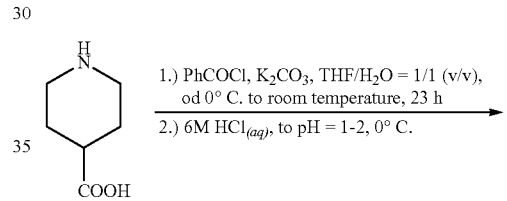

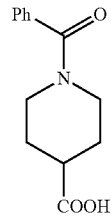

To a 250-mL round-bottomed flask equipped with a stirring bar, isonipecotic acid (10.000 g, 77.425 mmol) was added. THF (80 mL), H$_2$O (80 mL) and K$_2$CO$_3$ (53.504 g, 387.121 mmol) were added, and the mixture was cooled to 0° C. A solution of benzoyl chloride (8.980 mL, 77.425 mmol) in THF (35 mL) was added drop-wise. The reaction mixture was allowed to warm to r.t. and then stirred for 22 h. The reaction mixture was transferred into a 500-mL separating funnel and washed with EtOAc (3×150 mL). The aqueous phase was cooled to 0° C. and adjusted to pH 1-2 with 6 M aq HCl. The white precipitate was collected in a Büchner funnel under suction filtration, and then dried in vacuo at room temperature in the presence of NaOH, P$_2$O$_5$ and silica gel to constant mass to produce 15.369 g of 1-benzoylpiperidine-4-carboxylic acid. This product was used in the next step without further purification.

Product appearance: white solid
Yield: 85%
Melting point: 118-122° C.
TLC: R$_f$=0.55 (MeCN—H$_2$O-MeOH=3:1:1)

IR (ATR): 2857, 2359, 1730, 1612, 1447, 1207, 1169, 1014, 791, 731, 707, 628, 577. cm$^{-1}$ $^{1}$H NMR (400 MHz, DMSO-d6): δ=1.49 (2H, bs), 1.83 (2H, bd, J=45.68 Hz), 2.52-2.57 (1H, m), 3.01 (2H, bd, J=52.08 Hz), 3.52 (1H, bs), 4.31 (1H, bs), 7.34-7.46 (5H, m), 12.32 (1H, bs).

$^{13}$C NMR (100 MHz, DMSO-d6): δ=27.62, 28.24, 40.06, 40.74, 46.38, 126.61, 128.38, 129.31, 136.23, 168.96, 175.48.

HRMS (ESI$^{+}$): m/z calculated for $C_{13}H_{16}NO_3$: 234.1130; found 231.1125.

CHN analysis: Calculated for $C_{13}H_{15}NO_3$: C, 66.94; H, 6.48; N, 6.00. Found: C, 67.22; H, 6.78; N, 6.22.

Step 2: Synthesis of 1-benzoyl-N-(2-methoxyethyl) piperidine-4-carboxamide

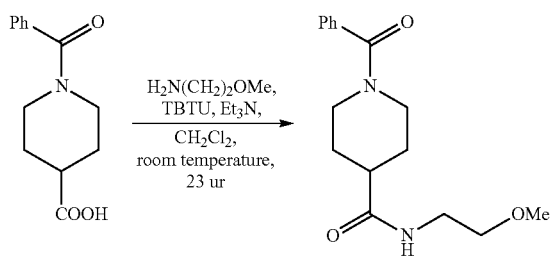 [SMILES: O=C(O)C1CCN(C(=O)c2ccccc2)CC1 ; COCCNC(=O)C1CCN(C(=O)c2ccccc2)CC1]

To a 250-mL round-bottomed flask equipped with a stirring bar, 12 (3.201 g, 13.723 mmol) and CH$_2$Cl$_2$ (180 mL) were added. Et$_3$N (3.824 mL, 27.446 mmol) was added drop-wise, followed by TBTU (4.406 g, 13.723 mmol). After 30 min, 2-methoxyethylamine (2.355 mL, 27.446 mmol) was added drop-wise, and the reaction mixture was stirred for 23 h. The reaction mixture was transferred into a 500-mL separating funnel and washed with H$_2$O (2×200 mL), 0.5 M aq HCl (2×200 mL), sat. aq NaHCO$_3$ solution (2×200 mL) followed by sat. brine solution (200 mL), dried over anhyd Na$_2$SO$_4$, and evaporated to produce 3.711 g of crude 1-benzoyl-N-(2-methoxyethyl)piperidine-4-carboxamide. This product was used in the next step without further purification.

Product appearance: white solid

HRMS (ESI$^{+}$): m/z calculated for $C_{16}H_{23}N_2O_3$: 291.1709; found: 291.1703.

Step 3: Sinteza N-((1-benzylpiperidin-4-yl)methyl)-2-methoxyethan-1-amine

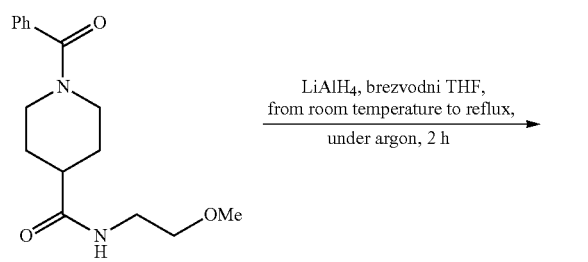

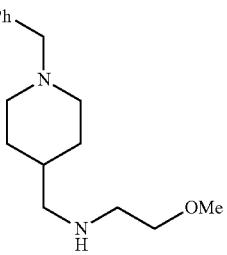

To a 250-mL tree-neck round-bottomed flask equipped with a stirring bar and a reflux condenser, LiAlH$_4$ (2.425 g, 63.904 mmol) was added under an argon atmosphere. Anhydrous THF (ca. 120 mL) was added with a double-tipped needle. A solution of crude 1-benzoyl-N-(2-methoxyethyl) piperidine-4-carboxamide (3.711 g, 12.781 mmol) in anhydrous THF (ca. 40 mL) was added with a double-tipped needle, and the reaction mixture was refluxed for 2 h. The mixture was then cooled to 0° C., and the excess hydride was decomposed by drop-wise addition of H$_2$O (2.425 mL) followed by 15% aq NaOH (2.425 mL) and then H$_2$O (7.275 mL). After vigorous stirring for 1 h at r.t., the mixture was filtered under suction and the white precipitate was washed thoroughly with THF (5×60 mL). The combined filtrates were evaporated to produce 2.833 g of crude N-((1-benzylpiperidin-4-yl)methyl)-2-methoxyethan-1-amine as a slightly golden liquid.

Product appearance: slightly golden liquid

HRMS (ESI$^{+}$): m/z calculated for $C_{16}H_{27}N_2O$: 263.2123; found: 263.2120.

Step 4: Synthesis of tert-butyl (1-benzylpiperidin-4-yl)methyl(2-methoxyethyl)carbamate

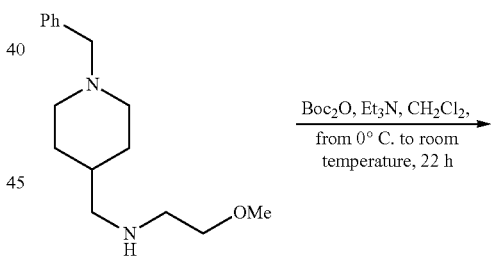

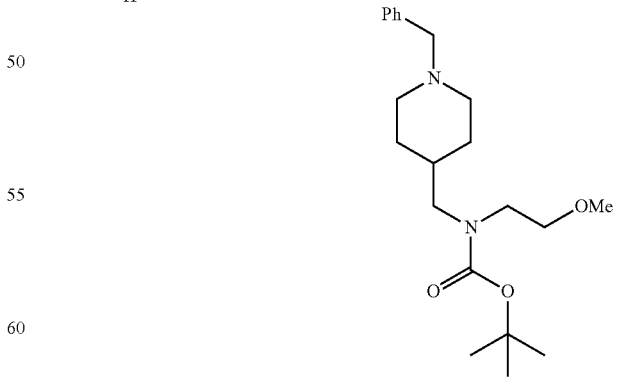

CH$_2$Cl$_2$ (50 mL) and a stirring bar were added to crude N-((1-benzylpiperidin-4-yl)methyl)-2-methoxyethan-1-amine (2,833 g, 10.797 mmol) in a 100-mL round-bottomed flask equipped with a stirring bar. Et$_3$N (1.505 mL, 10.797 mmol) was added drop-wise, and the reaction mixture was cooled to 0° C. A solution of Boc$_2$O (2.357 g, 10.797 mmol) in CH$_2$Cl$_2$ (10 mL) was added drop-wise, and the reaction mixture was allowed to warm to r.t. and then stirred for 22 h. The reaction mixture was transferred into a 100-mL separating funnel and washed with H$_2$O (30 mL), dried over anhyd Na$_2$SO$_4$, and evaporated. The residue was purified by flash column chromatography using CH$_2$Cl$_2$-MeOH (30:1) then CH$_2$Cl$_2$-MeOH (10:1) as the eluent to produce 3.254 g of tert-butyl (1-benzylpiperidin-4-yl)methyl(2-methoxyethyl)carbamate.

Product appearance: slightly golden oil
Yield: 65% (from 1-benzoylpiperidine-4-carboxylic acid)
TLC: R$_f$=0.52 (CH$_2$Cl$_2$-MeOH=10:1)
IR (ATR): 2923, 2801, 1689, 1411, 1364, 1147, 1117, 973, 872, 773, 737, 698, 568 cm$^{-1}$
$^1$H NMR (400 MHz, CDCl$_3$): δ=1.26-1.31 (2H, m), 1.44 (9H, s), 1.58-1.61 (3H, m), 1.89-1.95 (2H, m), 2.88-2.91 (2H, m), 3.14 (2H, d, J=6.90 Hz), 3.28-3.38 (5H, m), 3.43-3.50 (4H, m), 7.24-7.32 (5H, m).
$^{13}$C NMR (100 MHz, CDCl$_3$): δ=28.35, 29.93, 35.07, 35.49, 46.96, 47.66, 53.31, 53.49, 53.57, 58.72, 63.19, 63.39, 70.90, 71.09, 79.22, 79.31, 126.83, 128.03, 129.04, 129.16, 138.25, 138.43, 155.53, 155.69.
HRMS (ESI$^+$): m/z calculated for C$_{21}$H$_{35}$N$_2$O$_3$: 363.2648; found: 363.2648.
CHN analysis: calculated for C$_{21}$H$_{34}$N$_2$O$_3$: C, 69.58; H, 9.45; N, 7.73. Found: C, 69.66; H, 9.57; N, 7.69.

Step 5: Synthesis of tert-butyl (2-methoxyethyl)(piperidin-4-ylmethyl)carbamate

Pd(OH)$_2$ on carbon (20 wt. %) (0.828 g, 20% mass of -butyl (1-benzylpiperidin-4-yl)methyl(2-methoxyethyl)carbamate) was added, followed by cyclohexene (6.576 mL, 64,860 mmol). The resulting suspension was refluxed under an atmosphere of argon for 18 h, then filtered through a pad of Celite, and evaporated, to produce 1.696 g of crude tert-butyl (2-methoxyethyl)(piperidin-4-ylmethyl)carbamate. This product was used in the next step without further purification.

Product appearance: slightly golden oil
Yield: 96%
TLC: R$_f$=0.57 (CH$_2$Cl$_2$-MeOH-Et$_3$N=20:2:1, v/v/v)
HRMS (ESI$^+$): m/z calculated for C$_{14}$H$_{29}$N$_2$O$_3$: 273.2178; found: 273.2172.

Step 6: Synthesis of tert-butyl ((1-(2,3-dihydro-1H-inden-2-yl)piperidin-4-yl)methyl)(2-methoxyethyl)carbamate

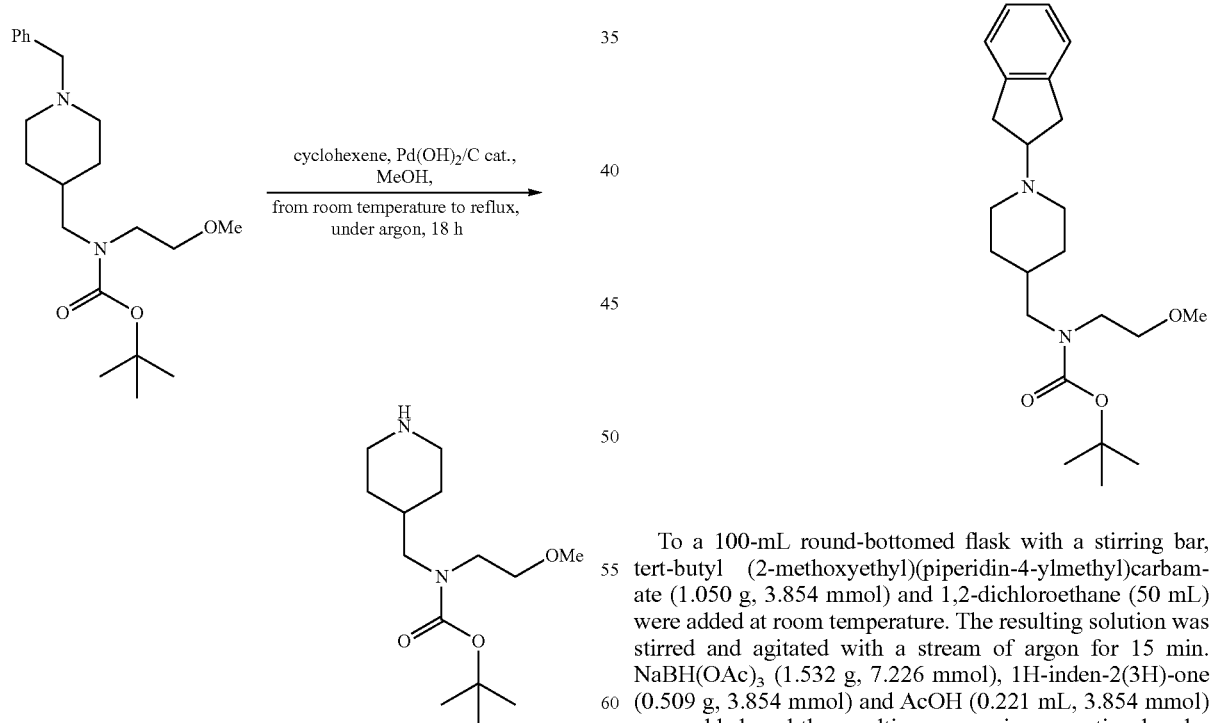

To a 100-mL round-bottomed flask with a stirring bar, tert-butyl (2-methoxyethyl)(piperidin-4-ylmethyl)carbamate (1.050 g, 3.854 mmol) and 1,2-dichloroethane (50 mL) were added at room temperature. The resulting solution was stirred and agitated with a stream of argon for 15 min. NaBH(OAc)$_3$ (1.532 g, 7.226 mmol), 1H-inden-2(3H)-one (0.509 g, 3.854 mmol) and AcOH (0.221 mL, 3.854 mmol) were added, and the resulting suspension was stirred under an atmosphere of argon for 72 h. The reaction mixture was opened to the air and quenched with saturated aqueous NaHCO$_3$ solution (50 mL). The mixture was transferred into a 250-mL separating funnel, and CH$_2$Cl$_2$ (20 mL) was added. The separating funnel was shaken vigorously and the organic phase was separated, dried over anhydrous Na$_2$SO$_4$, To a 250-mL round-bottomed flask with a stirring bar, tert-butyl (1-benzylpiperidin-4-yl)methyl(2-methoxyethyl)carbamate (2,351 g, 6,486 mmol) and MeOH (100 mL) were added at room temperature. The resulting solution was stirred and agitated with a stream of argon for 30 min.

and evaporated. The residue was purified by flash column chromatography using CH$_2$Cl$_2$/MeOH (30:1, v/v) as the eluent, to produce 1.198 g of tert-butyl ((1-(2,3-dihydro-1H-inden-2-yl)piperidin-4-yl)methyl)(2-methoxyethyl)carbamate.

Product appearance: slightly yellow solid
Yield: 80%
TLC: R$_f$=0.47 (CH$_2$Cl$_2$-MeOH=10:1, v/v)
IR (KBe): 2930, 2808, 1688, 1475, 1407, 1282, 1149, 1113, 1012, 979, 871, 745, 664 cm$^{-1}$
$^1$H-NMR (400 MHz, CDCl$_3$): δ=1.25-1.45 (11H, m), 1.68 (3H, d, J=12.3 Hz), 1.95-2.06 (2H, m), 2.88-2.93 (2H, m), 3.05-3.17 (7H, m), 3.34-3.39 (5H, m), 3.44-3.53 (2H, m), 7.11-7.18 (4H, m).
$^{13}$C-NMR (100 MHz, CDCl$_3$): δ=28.35, 29.82, 35.08, 35.39, 37.12, 46.92, 47.93, 51.48, 51.73, 53.54, 58.73, 67.11, 70.91, 71.08, 79.27, 79.37, 124.24, 126.24, 141.49, 155.53, 155.69 HRMS (ESI+): m/z calculated for C$_{23}$H$_{37}$N$_2$O$_3$: 389.2804; found: 389.2810.

Step 7: Synthesis of N-((1-(2,3-dihydro-1H-inden-2-yl)piperidin-4-yl)methyl)-2-methoxyethanamine di(2,2,2-trifluoroacetate)

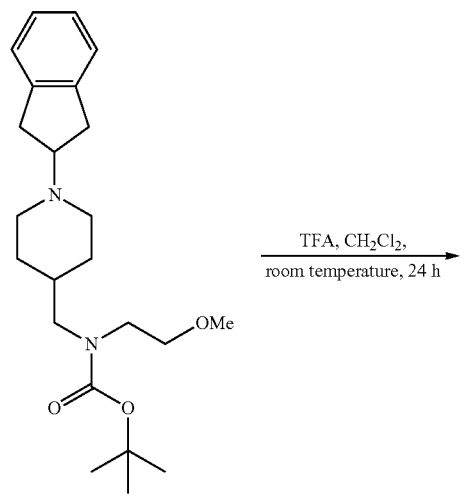

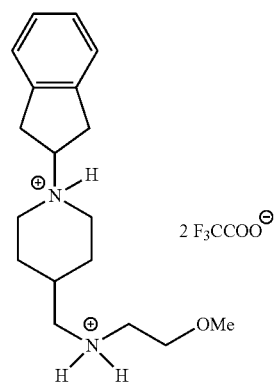

To a 100-mL round-bottomed flask equipped with a stirring bar, tert-butyl ((1-(2,3-dihydro-1H-inden-2-yl)piperidin-4-yl)methyl)(2-methoxyethyl)carbamate (1,100 g, 2.831 mmol) and CH$_2$Cl$_2$ (50 mL) were added at room temperature. The resulting solution was stirred and TFA (2.168 mL, 28,310 mmol) was added drop-wise. After 24 h, the reaction mixture was evaporated. The residue was co-evaporated with CH$_2$Cl$_2$ (2×40 mL), followed by n-hexane (2×50 mL). Et$_2$O (50 mL) was added to the oily residue, and the flask was placed in an ultrasonic bath for 15 min. During this time, the oily residue transformed into a white solid. The flask was removed from the ultrasonic bath and the precipitate was allowed to settle to the bottom of the flask. The supernatant was removed, Et$_2$O (30 mL) was added, and the flask was placed back in the ultrasonic bath for 1 min. The flask was removed from the ultrasonic bath and the precipitate was allowed to settle to the bottom of the flask. The supernatant was removed, Et$_2$O (30 mL) was added again, and this procedure was repeated two more times. After the final supernatant was removed, the solid residue was dried at reduced pressure to produce 1,272 g of crude N-((1-(2,3-dihydro-1H-inden-2-yl)piperidin-4-yl)methyl)-2-methoxyethanamine di(2,2,2-trifluoroacetate). This product was used in the next step without further purification.

Product appearance: white solid
Yield: 87%
HRMS (ESI+): m/z calculated for C$_{18}$H$_{29}$N$_2$O 289.2280; found 289.2286.

Step 8: Synthesis of N-((1-(2,3-dihydro-1H-inden-2-yl)piperidin-4-yl)methyl)-N-(2-methoxyethyl)naphthalene-2-sulfonamide

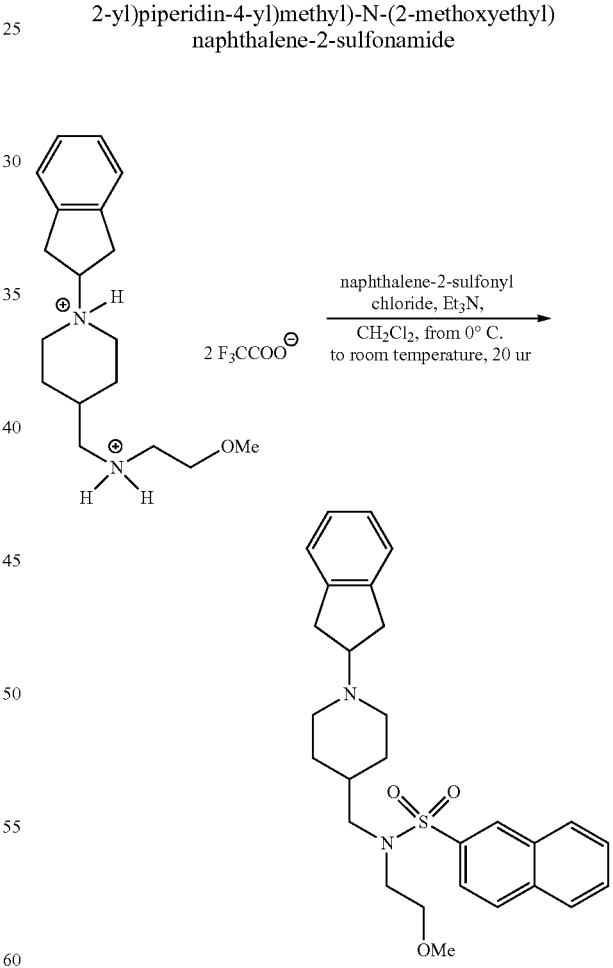

To a 25-mL round-bottomed flask equipped with a stirring bar, N-((1-(2,3-dihydro-1H-inden-2-yl)piperidin-4-yl)methyl)-2-methoxyethanamine di(2,2,2-trifluoroacetate) (0.250 g, 0.484 mmol) and CH$_2$Cl$_2$ (10 mL) were added at room temperature. The resulting suspension was stirred and Et$_3$N (0.202 mL, 1.452 mmol) was added drop-wise, followed by naphthalene-2-sulfonyl chloride (0,110 g, 0,484 mmol) and the reaction mixture was allowed to warm to r.t. and then stirred for 20 h. The reaction mixture was transferred into a 50-mL separating funnel, CH$_2$Cl$_2$ (15 mL) was added and washed with H$_2$O (20 mL), followed by saturated aqueous NaHCO$_3$ solution (20 mL). The organic phase was dried over anhyd Na$_2$SO$_4$, and evaporated. The residue was purified by flash column chromatography using CH$_2$Cl$_2$-MeOH (20:1, v/v) as the eluent to produce 0.208 g of N-((1-(2,3-dihydro-1H-inden-2-yl)piperidin-4-yl)methyl)-N-(2-methoxyethyl)naphthalene-2-sulfonamide.

Product appearance: white solid
Yield: 90%
TLC: R$_f$=0.48 (CH$_2$Cl$_2$/MeOH, 10:1, v/v)
IR (ATR)=2937, 1672, 1329, 1153, 1129, 1073, 999, 820, 743, 652, 617 cm$^{-1}$
$^1$H-NMR (400 MHz, CDCl$_3$): δ=1.57 (2H, bs), 1.89-1.92 (3H, m), 2.36 (2H, bs), 3.09-3.34 (13H, m), 3.48 (3H, t, J=5.5 Hz), 7.14-7.20 (4H, m), 7.60-7.67 (2H, m), 7.75-7.79 (1H, m), 7.89-7.98 (3H, m), 8.37 (1H, s).
$^{13}$C-NMR (400 MHz, CDCl$_3$): δ=28.35, 34.30, 36.06, 49.00, 50.98, 54.79, 58.68, 66.63, 71.31, 122.48, 124.31, 126.78, 127.53, 127.82, 128.49, 128.71, 129.14, 129.29, 132.08, 134.67, 135.97, 140.33.
HRMS (ESI+): m/z calculated for C$_{28}$H$_{35}$N$_2$O$_3$S: 479.2368; found: 479.2358.

The invention claimed is:
1. A compound having formula (II):

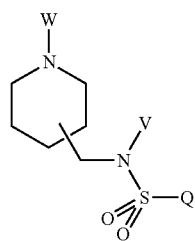

(II)

or a pharmaceutically acceptable salt thereof,
wherein:
the piperidine ring is 1,3-disubstituted;
W is

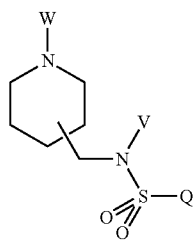

;

V is —H, —CH$_3$, —CH$_2$CH$_3$, —(CH$_2$)$_2$CH$_3$, —(CH$_2$)$_3$CH$_3$, —(CH$_2$)$_2$OCH$_3$ or —(CH$_2$)$_3$OCH$_3$; and
Q is

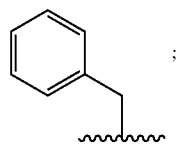 [SMILES: *Cc1ccccc1]

.

2. The compound of claim 1, wherein V is (CH$_2$)$_2$OCH$_3$ or —(CH$_2$)$_3$OCH$_3$.
3. The compound of claim 1, wherein V is (CH$_2$)$_2$OCH$_3$.
4. The compound of claim 1, wherein V is (CH$_2$)$_3$OCH$_3$.
5. A pharmaceutical composition comprising a pharmaceutically acceptable excipient and at least one compound having formula (II):

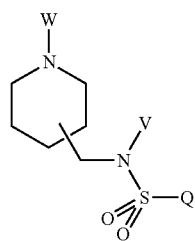

(II)

or a pharmaceutically acceptable salt thereof,
wherein:
the piperidine ring is 1,3-disubstituted or 1,4-disubstituted;
W is

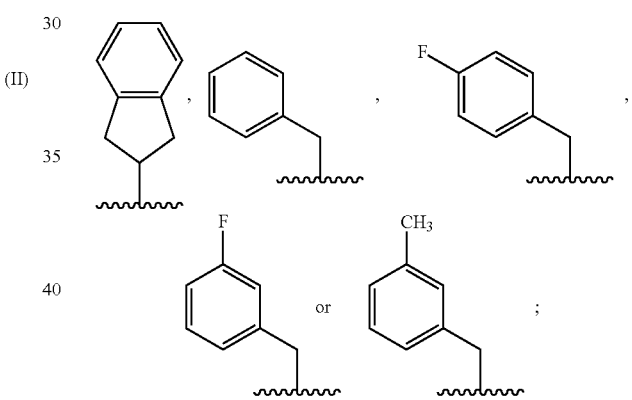

V is —H, —CH$_3$, —CH$_2$CH$_3$, —(CH$_2$)$_2$CH$_3$, —(CH$_2$)$_3$CH$_3$, —(CH$_2$)$_2$OCH$_3$ or —(CH$_2$)$_3$OCH$_3$; and
Q is

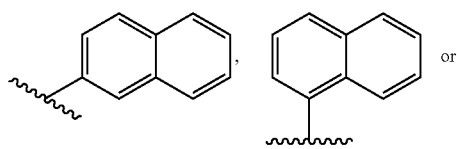

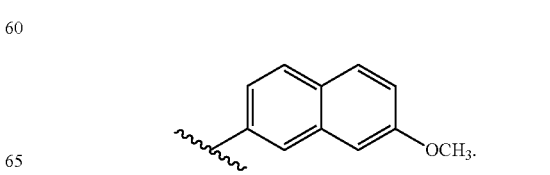

6. The pharmaceutical composition of claim 5, wherein:
the piperidine ring is 1,3-disubstituted;
W is

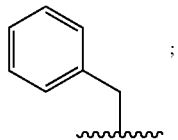 [SMILES: *Cc1ccccc1]

and
Q is

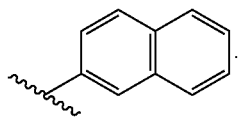 [SMILES: *c1ccc2ccccc2c1]

7. The pharmaceutical composition of claim 6, wherein V is —CH$_3$, —(CH$_2$)$_2$OCH$_3$ or —(CH$_2$)$_3$OCH$_3$.

8. The pharmaceutical composition of claim 5, wherein:
the piperidine ring is 1,4-disubstituted;
W is

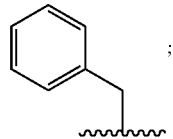 [SMILES: *Cc1ccccc1]

V is —(CH$_2$)$_2$OCH$_3$; and
Q is

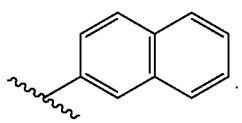 [SMILES: *c1ccc2ccccc2c1]

9. The pharmaceutical composition of claim 5, wherein:
the piperidine ring is 1,4-disubstituted;
W is

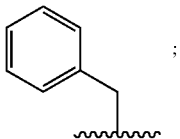 [SMILES: *Cc1ccccc1]

V is —(CH$_2$)$_3$OCH$_3$; and
Q is

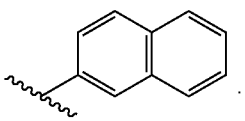 [SMILES: *c1ccc2ccccc2c1]

10. A method for modulating butyrylcholinesterase activity in a human or mammal, the method comprising administering to the human or mammal a therapeutically effective amount of a compound having formula (II):

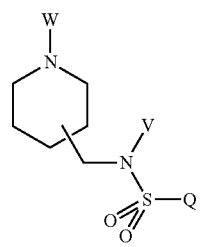

(II)

or a pharmaceutically acceptable salt thereof,
wherein:
the piperidine ring is 1,3-disubstituted or 1,4-disubstituted;
W is

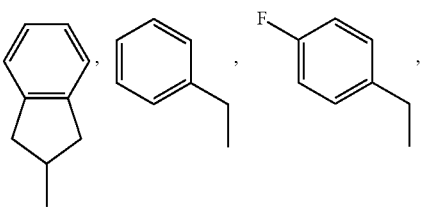

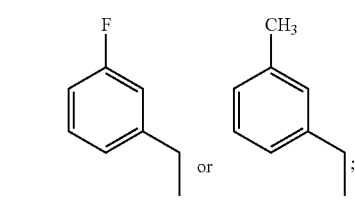

or

V is —H, —CH$_3$, —CH$_2$CH$_3$, —(CH$_2$)$_2$CH$_3$, —(CH$_2$)$_3$CH$_3$, —(CH$_2$)$_2$OCH$_3$ or —(CH$_2$)$_3$OCH$_3$;
and
Q is

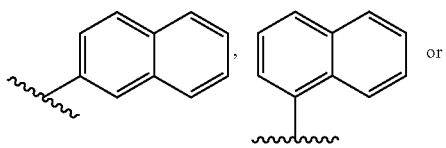

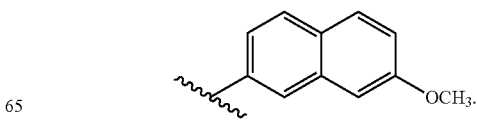

11. The method of claim 10, wherein:
the piperidine ring is 1,3-disubstituted;
W is

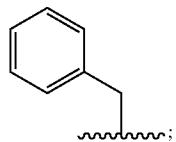 [SMILES: *Cc1ccccc1]

and
Q is

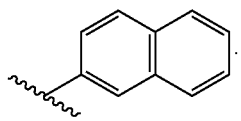

12. The method of claim 11, wherein V is —CH$_3$, —(CH$_2$)$_2$OCH$_3$ or —(CH$_2$)$_3$OCH$_3$.
13. The method of claim 11, wherein V is —CH$_3$.
14. The method of claim 11, wherein V is (CH$_2$)$_2$OCH$_3$.
15. The method of claim 11, wherein V is (CH$_2$)$_3$OCH$_3$.
16. The method of claim 10, wherein:
the piperidine ring is 1,4-disubstituted;
W is

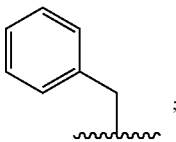 [SMILES: *Cc1ccccc1]

V is —(CH$_2$)$_2$OCH$_3$; and
Q is

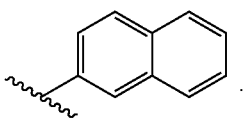 [SMILES: *c1ccc2ccccc2c1]

17. The method of claim 10, wherein:
the piperidine ring is 1,4-disubstituted;
W is

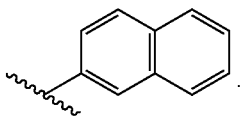 [SMILES: *c1ccc2ccccc2c1]

V is —(CH$_2$)$_3$OCH$_3$; and
Q is

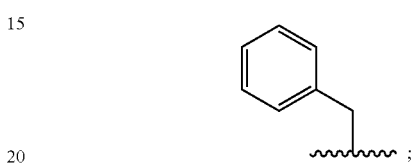

18. The method of claim 1, wherein the human or mammal has a disease or disorder selected from the group consisting of Alzheimer's disease, multiple sclerosis and dementia.

19. The method of claim 1, wherein the human or mammal has a disease or disorder selected from the group consisting of Alzheimer's disease and dementia.

* * * * *

UNITED STATES PATENT AND TRADEMARK OFFICE
CERTIFICATE OF CORRECTION

PATENT NO. : 10,071,964 B2
APPLICATION NO. : 15/560580
DATED : September 11, 2018
INVENTOR(S) : Brus et al.

Page 1 of 1

It is certified that error appears in the above-identified patent and that said Letters Patent is hereby corrected as shown below:

In the Claims

Column 60, Line 30 to Line 40: Claim 10, Delete " W is 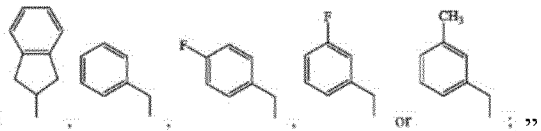 "

and insert -- W is 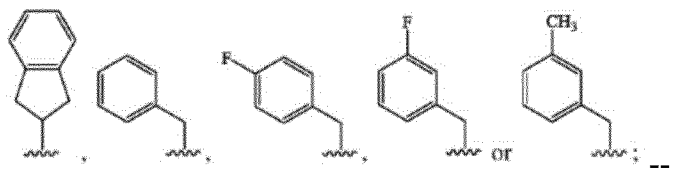 --

Column 62, Line 32: Claim 18, Delete "claim 1" and insert -- claim 5 --

Column 62, Line 36: Claim 19, Delete "claim 1" and insert -- claim 5 --

Signed and Sealed this
Sixth Day of November, 2018

Andrei Iancu
*Director of the United States Patent and Trademark Office*